(12) United States Patent  (10) Patent No.: US 9,152,042 B2
Nakayama et al.  (45) Date of Patent: Oct. 6, 2015

(54) ACRYLIC ESTER DERIVATIVE, HIGH-MOLECULAR COMPOUND AND PHOTORESIST COMPOSITION

(75) Inventors: Osamu Nakayama, Niigata (JP); Manabu Yada, Niigata (JP)

(73) Assignee: KURARAY CO., LTD., Kurashiki-shi (JP)

( * ) Notice: Subject to any disclaimer, the term of this patent is extended or adjusted under 35 U.S.C. 154(b) by 81 days.

(21) Appl. No.: 13/820,855

(22) PCT Filed: Sep. 2, 2011

(86) PCT No.: PCT/JP2011/070034
§ 371 (c)(1),
(2), (4) Date: Mar. 5, 2013

(87) PCT Pub. No.: WO2012/033019
PCT Pub. Date: Mar. 15, 2012

(65) Prior Publication Data
US 2013/0164675 A1  Jun. 27, 2013

(30) Foreign Application Priority Data
Sep. 8, 2010  (JP) .................................. 2010-201033

(51) Int. Cl.
| | | |
|---|---|---|
| G03F 7/004 | (2006.01) | |
| C07D 209/56 | (2006.01) | |
| C07D 327/04 | (2006.01) | |
| C07D 307/00 | (2006.01) | |
| C07D 493/08 | (2006.01) | |
| C07D 497/18 | (2006.01) | |
| G03F 7/039 | (2006.01) | |
| C08F 220/36 | (2006.01) | |
| C08F 220/28 | (2006.01) | |
| C08F 220/18 | (2006.01) | |

(52) U.S. Cl.
CPC .............. *G03F 7/004* (2013.01); *C07D 209/56* (2013.01); *C07D 307/00* (2013.01); *C07D 327/04* (2013.01); *C07D 493/08* (2013.01); *C07D 497/18* (2013.01); *C08F 220/36* (2013.01); *G03F 7/0397* (2013.01); *C08F 220/28* (2013.01); *C08F 2220/1833* (2013.01)

(58) Field of Classification Search
None
See application file for complete search history.

(56) References Cited

U.S. PATENT DOCUMENTS

| | | | |
|---|---|---|---|
| 8,314,258 B2 | 11/2012 | Nakayama et al. | |
| 8,362,169 B2 | 1/2013 | Nakayama et al. | |
| 2002/0051933 A1* | 5/2002 | Kodama et al. | 430/270.1 |
| 2009/0226842 A1* | 9/2009 | Shimizu et al. | 430/281.1 |
| 2010/0086873 A1* | 4/2010 | Seshimo et al. | 430/281.1 |
| 2010/0323296 A1* | 12/2010 | Ichikawa et al. | 430/286.1 |
| 2010/0331508 A1 | 12/2010 | Sato et al. | |
| 2011/0117497 A1 | 5/2011 | Sato et al. | |
| 2013/0005990 A1 | 1/2013 | Nakayama et al. | |

FOREIGN PATENT DOCUMENTS

| | | |
|---|---|---|
| JP | 11 109628 | 4/1999 |
| JP | 2000 26446 | 1/2000 |

(Continued)

OTHER PUBLICATIONS

Machine translation JP 2010-091638. Apr. 22, 2010.*
Henbest, H. B. et al., "Aspects of Stereochemistry. Part XI. Epoxide Formation in the cycloHexene and bicycloHeptene Series," Journal of the Chemical Society, pp. 221 to 226, (1959).

(Continued)

*Primary Examiner* — Cynthia H Kelly
*Assistant Examiner* — Alyssa L Cepluch
(74) *Attorney, Agent, or Firm* — Oblon, McClelland, Maier & Neustadt, L.L.P.

(57) ABSTRACT

The invention provides a novel acrylic ester derivative which can form a structural unit of a polymer to be incorporated into a photoresist composition; a polymer produced through polymerization of a raw material containing the acrylic ester derivative; and a photoresist composition which contains the polymer and which, as compared with the case of conventional ones, realizes formation of a high-resolution resist pattern having improved LWR. Specifically, the present invention provides, for example, an acrylic ester derivative represented by the following formula (1):

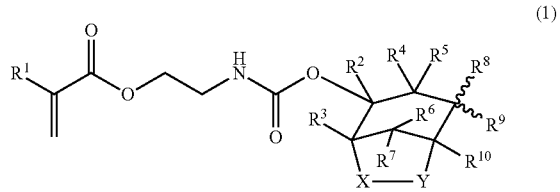

(1)

wherein $R^1$ represents a hydrogen atom, a methyl group, or a trifluoromethyl group; each of $R^2$, $R^3$, $R^5$, $R^7$, $R^8$, and $R^{10}$ represents a hydrogen atom, an alkyl group, a cycloalkyl group, or an alkoxy group; each of $R^4$ and $R^6$ represents a hydrogen atom, an alkyl group, a cycloalkyl group, or an alkoxy group, or $R^4$ and $R^6$ are linked together to form an alkylene group, —O—, or —S—; $R^9$ represents a hydrogen atom, an alkyl group, a cycloalkyl group, an alkoxy group, or —COOR$^{11}$; $R^{11}$ represents an alkyl group; X represents —O— or >N—R$^{12}$; $R^{12}$ represents a hydrogen atom or an alkyl group; Y represents >C=O or >S(=O)$_n$; n is an integer of 0 to 2; and the wavy lines represent that either $R^8$ or $R^9$ may be in an endo or exo position.

20 Claims, No Drawings

(56) References Cited

FOREIGN PATENT DOCUMENTS

| | | | |
|---|---|---|---|
| JP | 2000 47386 | | 2/2000 |
| JP | 2001 188346 | | 7/2001 |
| JP | 2007 31355 | | 2/2007 |
| JP | 2010091638 A | * | 4/2010 |
| JP | 2010-168523 A | | 8/2010 |
| WO | 2010 001913 | | 1/2010 |

OTHER PUBLICATIONS

Distler, V. et al., "Zur Chemie der Vinylsulfonsaure," Angewandte Chemie, vol. 77 (7), pp. 291 to 302, (1965).

International Search Report Issued Nov. 15, 2011 in PCT/JP11/70034 Filed Sep. 2, 2011.

Japanese Office Action issued Dec. 16, 2014 in Patent Application No. 2012-532959 (without English Translation).

* cited by examiner

ACRYLIC ESTER DERIVATIVE, HIGH-MOLECULAR COMPOUND AND PHOTORESIST COMPOSITION

This application is a 371 of PCT/JP11/70034, filed Sep. 2, 2011. Priority to Japanese patent application 2010-201033, filed Sep. 8, 2010, is claimed.

TECHNICAL FIELD

The present invention relates to an acrylic ester derivative; a polymer produced through polymerization of a raw material containing the acrylic ester derivative; and a photoresist composition which realizes formation of a high-resolution resist pattern having improved line width roughness (LWR).

BACKGROUND ART

Lithography involves a process in which, for example, a resist film is formed from a resist material on, a substrate; the resist film is selectively exposed to a radiation such as light or an electron beam via a mask having a specific pattern; and the exposed resist film is developed, to thereby form a specific resist pattern on the film. As used herein, the term "positive tone resist material" refers to a resist material which, when exposed to light, dissolves in a developer, and the term "negative tone resist material" refers to a resist material which, when exposed to light, does not dissolve in a developer.

In recent years, with the progress of lithography techniques, micro-patterning has been rapidly developed in production of semiconductor devices or liquid crystal display devices. Generally, miniaturization of patterning is carried out by use of an exposure light source of short wavelength (higher energy). Hitherto, ultraviolet rays such as g-ray and i-ray have been used for lithography. Recently, KrF excimer laser or ArF excimer laser has been used for mass production of semiconductor devices. Also, attempts have been made to use, in lithography, $F_2$ excimer laser, electron beams, EUVs (extreme ultraviolet rays), X-rays, etc. having a shorter wavelength (higher energy) as compared with KrF excimer laser or ArF excimer laser.

A resist material is required to exhibit various lithographic properties, including sensitivity to such an exposure light source, and resolution which realizes reproduction of micro-patterning. A resist material satisfying these requirements is, for example, a chemically amplified resist composition containing a base component whose solubility in an alkaline developer changes through the action of an acid, and an acid generator component which generates an acid through light exposure.

For example, a generally used chemically amplified positive tone resist composition contains a resin component (base resin) whose solubility in an alkaline developer increases through the action of an acid, and an acid generator component. In the case where a resist film is formed from such a resist composition, when the resist film is subjected to selective light exposure during formation of a resist pattern, an acid is generated from the photoacid generator component at an exposed portion of the film, and the solubility of the resin component in an alkaline developer increases through the action of the acid, whereby the exposed portion becomes soluble in the alkaline developer.

A photoresist composition which is currently used for, for example, ArF excimer laser lithography generally contains, as a base resin component, a resin having a main chain formed of a structural unit derived from a (meth)acrylric ester; i.e., an acrylic resin, since the resin exhibits excellent transparency at 193 nm or thereabout. As has been known, a photoresist composition containing a polymer containing a structural unit having norbornane lactone exhibits high etching resistance and improved adhesion to a substrate (see Patent Document 1). There has also been proposed, for example, a polymer for a photoresist composition, the polymer containing a structural unit having a norbornane lactone skeleton or norbornane sultone skeleton to which an acryloyloxy group is bonded via a linkage group (see Patent Document 2 or 3).

PRIOR ART DOCUMENT

Patent Document

Patent Document 1: Japanese Patent Application Laid-Open ( ) No. 2000-26446
Patent Document 2: Japanese Patent Application Laid-Open ( ) No. 2001-188346
Patent Document 3: International Patent Publication WO 2010/001913

SUMMARY OF THE INVENTION

Problems to be Solved by the Invention

As described above, in recent years, with the progress of lithography techniques, micro-patterning has been rapidly developed in production of semiconductor devices or liquid crystal display devices. In connection therewith, keen demand has arisen for development of a resist material which realizes further improved lithographic properties, including resolution and line width roughness (LWR), as well as further improved patterning. Therefore, an important task is to develop a novel acrylic ester derivative which can form a structural unit of a polymer to be incorporated into a photoresist composition.

In view of the foregoing, an object of the present invention is to provide a novel acrylic ester derivative which can form a structural unit of a polymer to be incorporated into a photoresist composition. Another object of the present invention is to provide a polymer produced through polymerization of a raw material containing the acrylic ester derivative. Yet another object of the present invention is to provide a photoresist composition which contains the polymer and which, as compared with the case of conventional ones, realizes formation of a high-resolution resist pattern having improved LWR.

Means for Solving the Problems

The present inventors have conducted extensive studies, and as a result have found that a photoresist composition containing a polymer produced through polymerization of a raw material containing a specific acrylic ester derivative realizes formation of a high-resolution resist pattern having improved LWR, as compared with the case of conventional photoresist compositions.

Accordingly, the present invention provides the following [1] to [5].

[1] An acrylic ester derivative represented by the following formula (1):

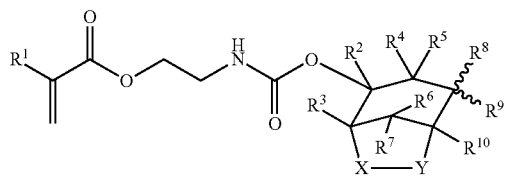

(wherein $R^1$ represents a hydrogen atom, a methyl group, or a trifluoromethyl group; each of $R^2$, $R^3$, $R^5$, $R^7$, $R^8$, and $R^{10}$ represents a hydrogen atom, a C1 to C6 alkyl group, a C3 to C6 cycloalkyl group, or a C1 to C6 alkoxy group; each of $R^4$ and $R^6$ represents a hydrogen atom, a C1 to C6 alkyl group, a C3 to C6 cycloalkyl group, or a C1 to C6 alkoxy group, or $R^4$ and $R^6$ are linked together to form a C1 to C3 alkylene group, —O—, or —S—; $R^9$ represents a hydrogen atom, a C1 to C6 alkyl group, a C3 to C6 cycloalkyl group, a C1 to C6 alkoxy group, or —COOR$^{11}$; $R^{11}$ represents a C1 to C3 alkyl group; X represents —O— or >N—R$^{12}$ (i.e., —N(R$^{12}$)—); R$^{12}$ represents a hydrogen atom or a C1 to C5 alkyl group; Y represents >C=O (i.e., —C(=O)—) or >S(=O)$_n$ (i.e., —S(=O)$_n$—); n is an integer of 0 to 2; and the wavy lines represent that either $R^8$ or $R^9$ may be in an endo or exo position).

[2] An acrylic ester derivative according to [1] above, which is represented by the following formula (1'):

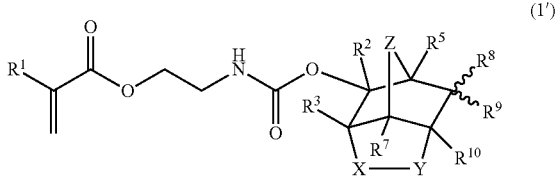

(wherein $R^1$, $R^2$, $R^3$, $R^5$, $R^7$, $R^8$, $R^9$, $R^{10}$, X, Y, and the wavy lines are as defined above; and Z represents a methylene group, —O—, or —S—).

[3] A polymer produced through polymerization of a raw material containing an acrylic ester derivative as recited in [1] or [2] above.

[4] A photoresist composition comprising a polymer as recited in [3] above, a photoacid generator, and a solvent.

[5] A method for producing an acrylic ester derivative as recited in [1] or [2] above, the method comprising causing an isocyanate derivative represented by the following formula (2) to react with an alcohol derivative represented by the following formula (3) at −30 to 100° C.:

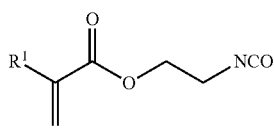

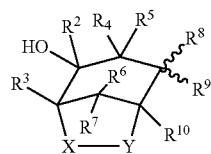

(wherein $R^1$ to $R^{10}$, X, Y, and the wavy lines are as defined above).

Effects of the Invention

A photoresist composition containing a polymer produced through polymerization of a raw material containing the acrylic ester derivative of the present invention realizes formation of a high-resolution resist pattern having improved LWR.

MODES FOR CARRYING OUT THE INVENTION

[Acrylic Ester Derivative (1)]

An acrylic ester derivative represented by the following formula (1) (hereinafter may be referred to as "acrylic ester derivative (1)") is useful for producing a photoresist composition which realizes improvement of LWR.

A characteristic feature of acrylic ester derivative (1) resides in that it has a specific cyclic structure at the molecular end, and also has the carbamate bond connected to an ethylene group. A photoresist composition containing a polymer produced through polymerization of a raw material containing the acrylic ester derivative realizes formation of a high-resolution resist pattern having improved LWR, as compared with the case of conventional photoresist compositions. The reason why the effects of the present invention are obtained has not yet been elucidated. However, a conceivable reason is that the length of diffusion of an acid generated from a photoacid generator is appropriately reduced through interaction between the acid and both a polar group cyclically bonded to the norbornane ring of the acrylic ester derivative (1) of the present invention and a polar carbamate bond connecting the norbornane ring with a polymerizable group.

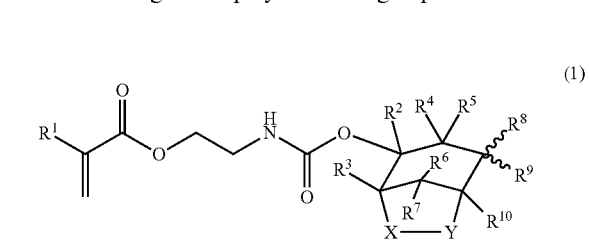

$R^1$ represents a hydrogen atom, a methyl group, or a trifluoromethyl group. Of these, a hydrogen atom or a methyl group is preferred.

Each of $R^2$, $R^3$, $R^5$, $R^7$, $R^8$, and $R^{10}$ represents a hydrogen atom, a C1 to C6 alkyl group, a C3 to C6 cycloalkyl group, or a C1 to C6 alkoxy group.

Examples of the C1 to C6 alkyl group, which may be in linear or branched form, include methyl, ethyl, n-propyl, isopropyl, n-butyl, isobutyl, s-butyl, n-pentyl, and n-hexyl. Of these, C1 to C3 alkyl groups are preferred.

Examples of the C3 to C6 cycloalkyl group include cyclopropyl, cyclobutyl, cyclopentyl, and cyclohexyl.

Examples of the C1 to C6 alkoxy group, which may be in linear or branched form, include methoxy, ethoxy, n-propoxy, isopropoxy, n-butoxy, isobutoxy, t-butoxy, n-pentyloxy, and n-hexyloxy. Of these, C1 to C3 alkoxy groups are preferred.

Each of $R^2$, $R^3$, $R^5$, $R^7$, $R^8$, and $R^{10}$ is preferably a hydrogen atom, a C1 to C3 alkyl group, or a C1 to C3 alkoxy group, more preferably a hydrogen atom.

Each of $R^4$ and $R^6$ represents a hydrogen atom, a C1 to C6 alkyl group, a C3 to C6 cycloalkyl group, or a C1 to C6 alkoxy group; or $R^4$ and $R^6$ are linked together to form a C1 to C3 alkylene group, —O—, or —S—.

Examples of the C1 to C6 alkyl group, which may be in linear or branched form, include methyl, ethyl, n-propyl, isopropyl, n-butyl, isobutyl, s-butyl, n-pentyl, and n-hexyl. Of these, C1 to C3 alkyl groups are preferred.

Examples of the C3 to C6 cycloalkyl group include cyclopropyl, cyclobutyl, cyclopentyl, and cyclohexyl.

Examples of the C1 to C6 alkoxy group, which may be in linear or branched form, include methoxy, ethoxy, n-propoxy, isopropoxy, n-butoxy, isobutoxy, t-butoxy, n-pentyloxy, and n-hexyloxy. Of these, C1 to C3 alkoxy groups are preferred.

Examples of the C1 to C3 alkylene group formed through linking between $R^4$ and $R^6$ include methylene, ethane-1,1-diyl, ethane-1,2-diyl, propane-1,1-diyl, propane-1,2-diyl, propane-1,3-diyl, and propane-2,2-diyl. Of these, a methylene group and an ethane-1,2-diyl group are preferred, with a methylene group being more preferred.

For improvement of LWR and resolution, preferably, $R^4$ and $R^6$ are linked together to form a C1 to C3 alkylene group, —O—, or —S—, more preferably, a methylene group; i.e., a C1 alkylene group, —O—, or —S—. That is, the acrylic ester derivative is more preferably one represented by the following formula (1'):

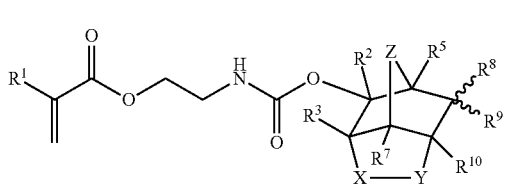

(1')

(wherein $R^1$, $R^2$, $R^3$, $R^5$, $R^7$, $R^8$, $R^9$, $R^{10}$, X, Y, and the wavy lines are as defined above or below; and Z represents a methylene group, —O—, or —S—).

$R^9$ represents a hydrogen atom, a C1 to C6 alkyl group, a C3 to C6 cycloalkyl group, a C1 to C6 alkoxy group, or —COOR$^{11}$; and $R^{11}$ represents a C1 to C3 alkyl group.

Examples of the C1 to C6 alkyl group, which may be in linear or branched form, include methyl, ethyl, n-propyl, isopropyl, n-butyl, isobutyl, s-butyl, n-pentyl, and n-hexyl. Of these, C1 to C3 alkyl groups are preferred.

Examples of the C3 to C6 cycloalkyl group include cyclopropyl, cyclobutyl, cyclopentyl, and cyclohexyl.

Examples of the C1 to C6 alkoxy group, which may be in linear or branched form, include methoxy, ethoxy, n-propoxy, isopropoxy, n-butoxy, isobutoxy, t-butoxy, n-pentyloxy, and n-hexyloxy. Of these, C1 to C3 alkoxy groups are preferred.

Examples of the C1 to C3 alkyl group represented by $R^{11}$ include methyl, ethyl, n-propyl, and isopropyl.

X represents —O— or >N—R$^{12}$, and $R^{12}$ represents a hydrogen atom or a C1 to C5 alkyl group. Examples of the C1 to C5 alkyl group represented by $R^{12}$, which may be in linear or branched form, include methyl, ethyl, n-propyl, isopropyl, n-butyl, isobutyl, s-butyl, t-butyl, and n-pentyl. Of these, C1 to C4 alkyl groups are preferred, and branched C3 or C4 alkyl groups are more preferred, with a t-butyl group being much more preferred. $R^{12}$ is preferably a hydrogen atom or a t-butyl group.

Y represents >C=O or >S(=O)$_n$, and n is an integer of 0 to 2. The integer n is preferably 1 or 2, more preferably 2.

No particular limitation is imposed on the combination of X and Y. When X is —O—, Y may be >C=O or >S(=O)$_n$, whereas when X is >N—R$^{12}$, Y may be >C=O or >S(=O)$_n$.

In formula (1) or (1'), the wavy lines represent that either $R^8$ or $R^9$ may be in an endo or exo position. Particularly preferably, $R^9$ is in an endo position.

Specific examples of the acrylic ester derivative (1) are described below. However, the acrylic ester derivative (1) is not particularly limited to the below-described examples.

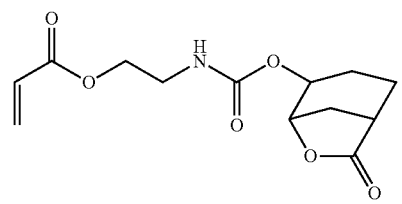

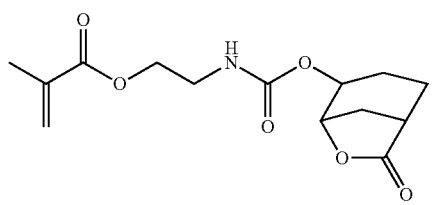

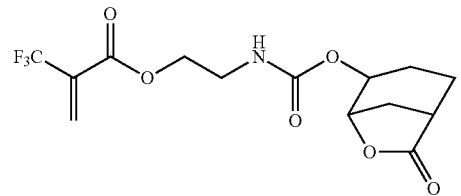

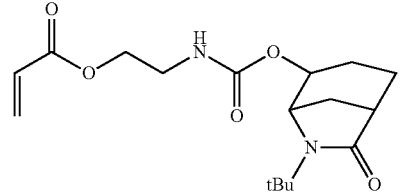

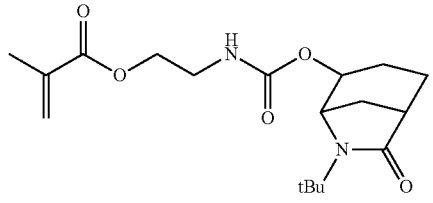

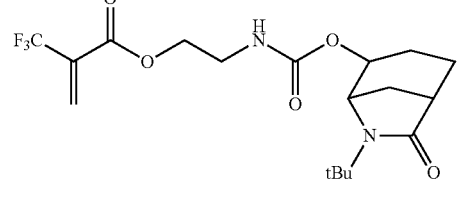

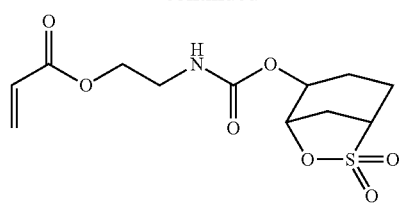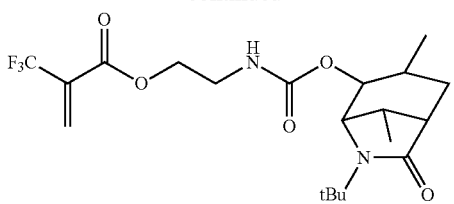

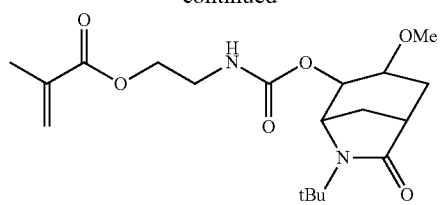
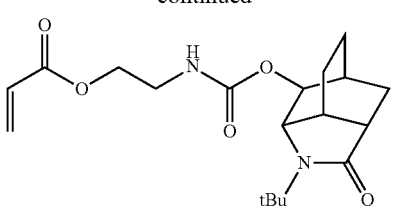
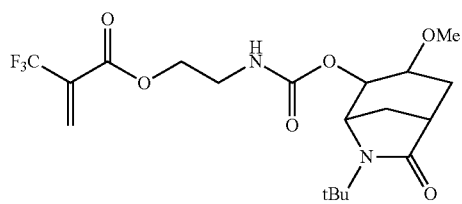
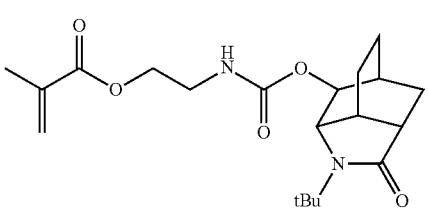
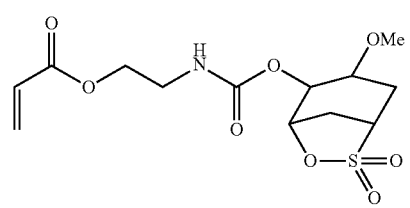
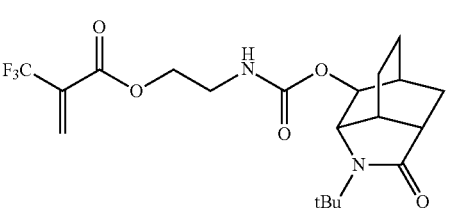
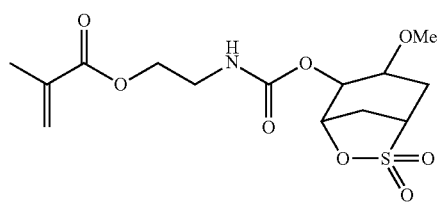
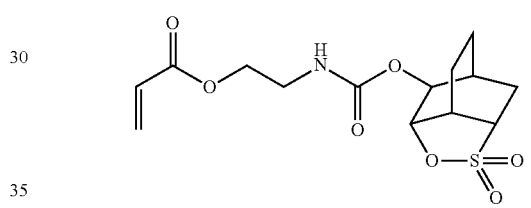
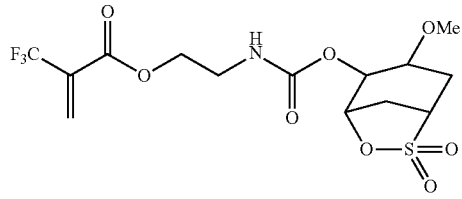
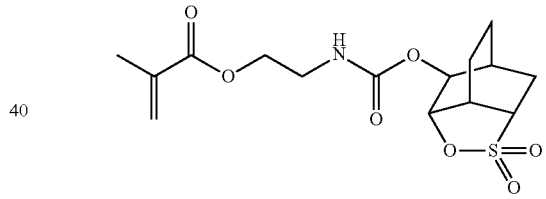
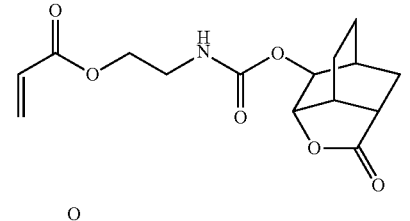
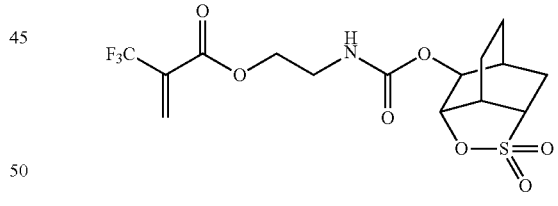
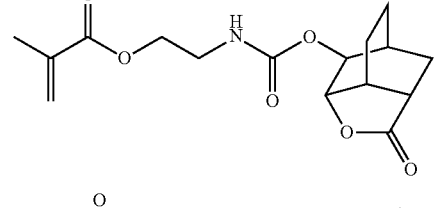
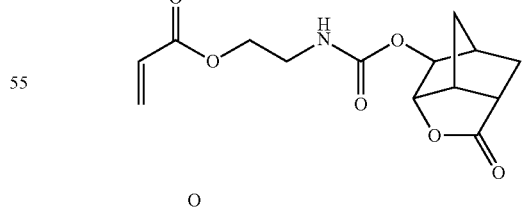
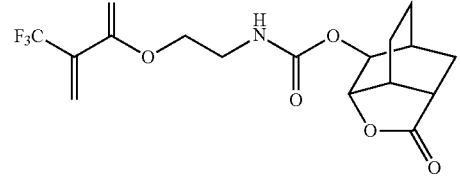
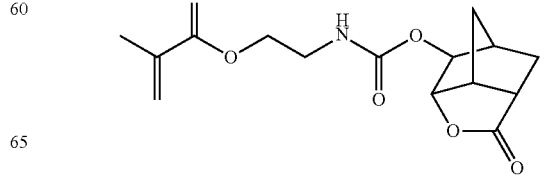

11
-continued
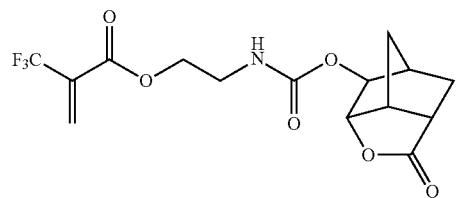
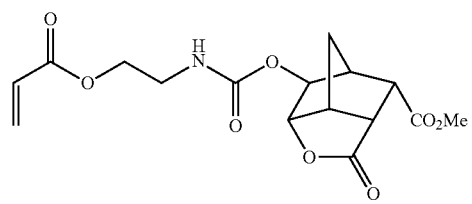
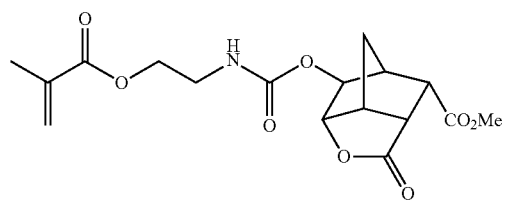
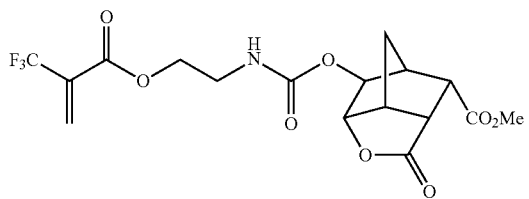
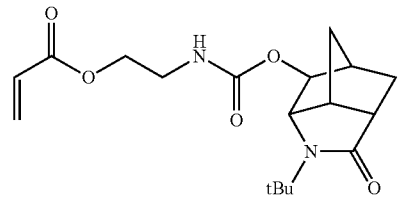
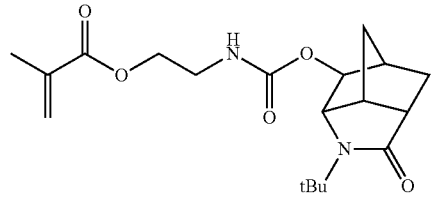
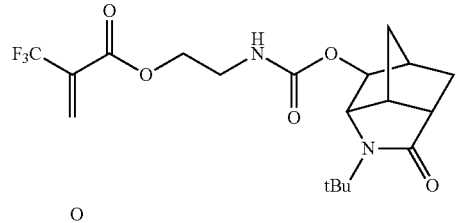
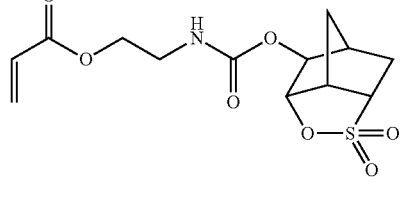
12
-continued
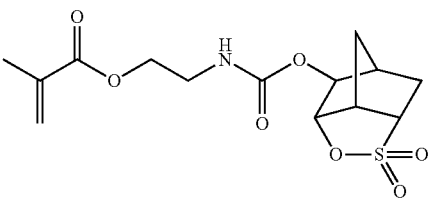
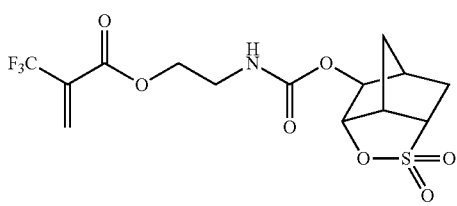
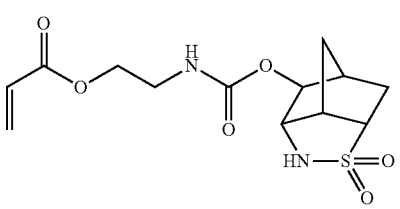
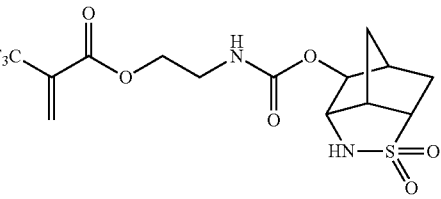
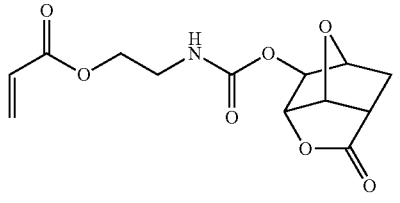
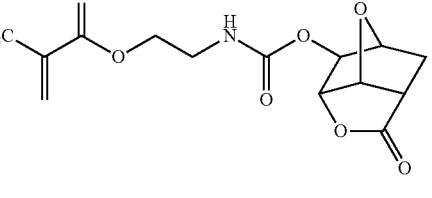

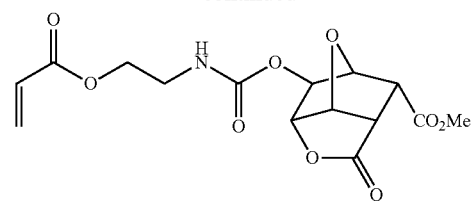
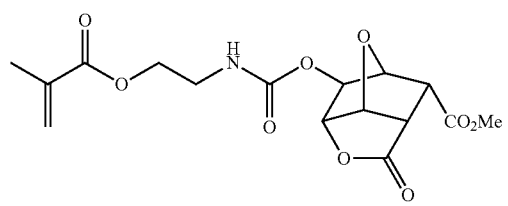
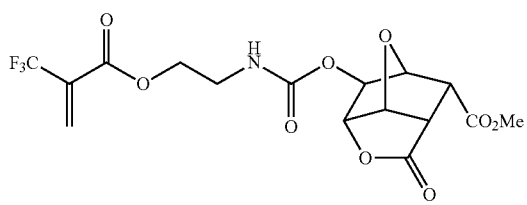
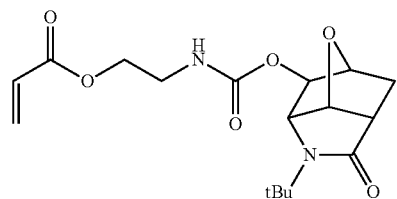
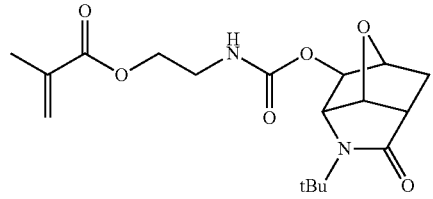
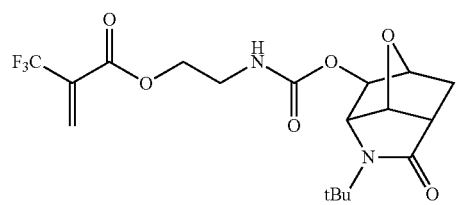
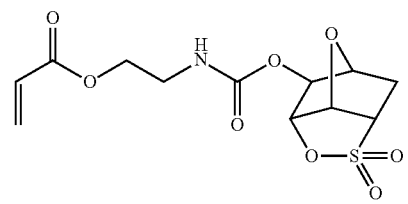
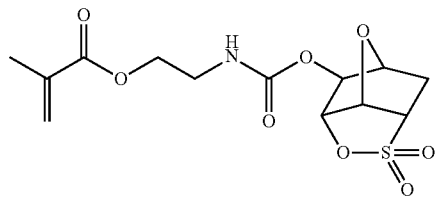
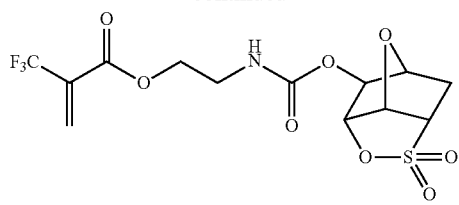
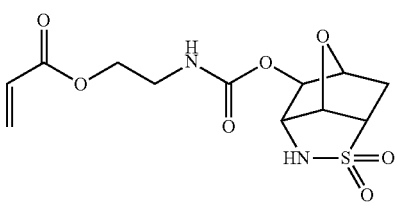
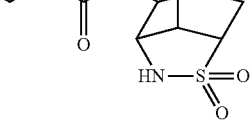
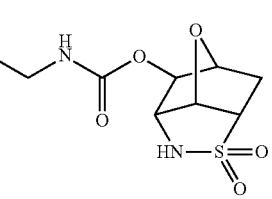
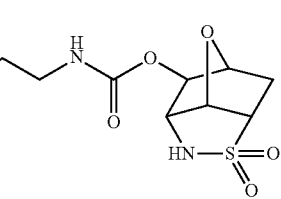
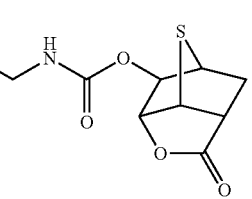
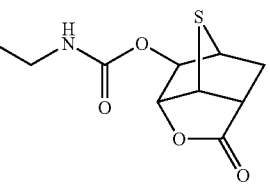
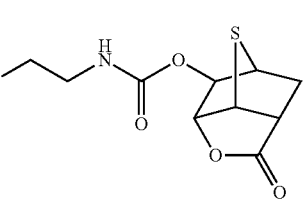
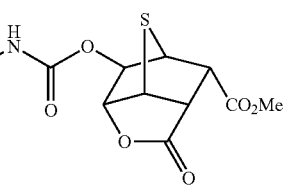

-continued

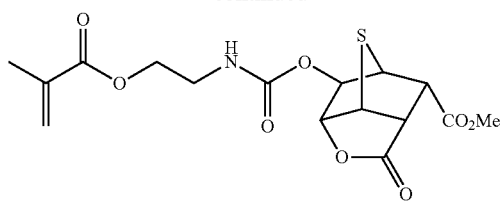
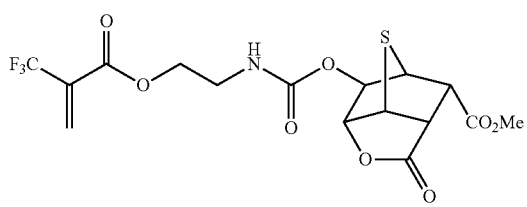
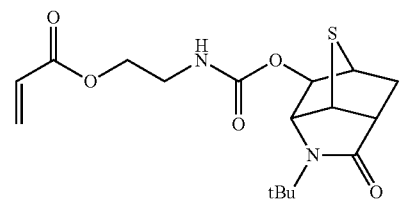
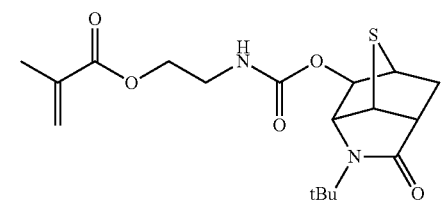
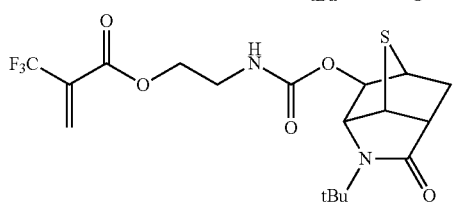
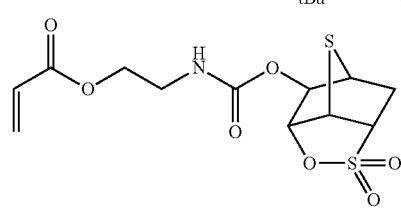
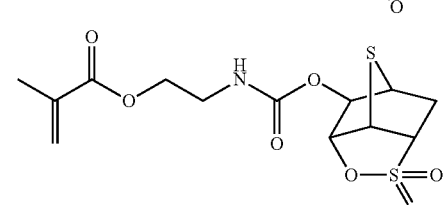
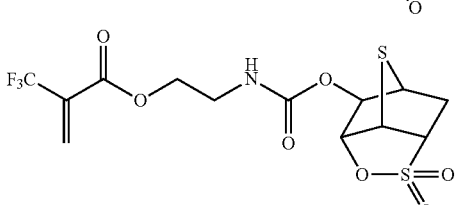

-continued

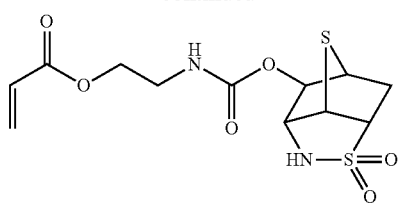
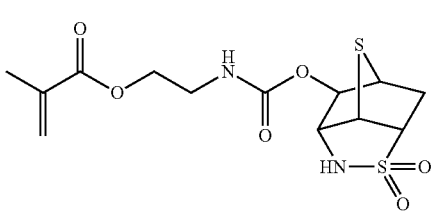
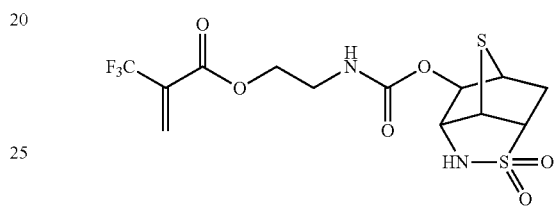

In order to produce a photoresist composition which realizes improvement of LWR, in an acrylic ester derivative (1), preferably, $R^1$ is a hydrogen atom or a methyl group; each of $R^2$, $R^3$, $R^5$, $R^7$, $R^8$, and $R^{10}$ is a hydrogen atom; $R^9$ is a hydrogen atom or —$COOR^{11}$ ($R^{11}$ is a methyl group); $R^4$ and $R^6$ are linked together to form a methylene group or —O— (i.e., Z is a methylene group or —O—); X is —O— or >N—$R^{12}$; when X is >N—$R^{12}$, $R^{12}$ is a hydrogen atom or a t-butyl group; Y is >C=O or >S(=O)$_n$; and when Y is >S(=O)$_n$, n is 2.

More preferred is an acrylic ester derivative represented by any of the following formulas:

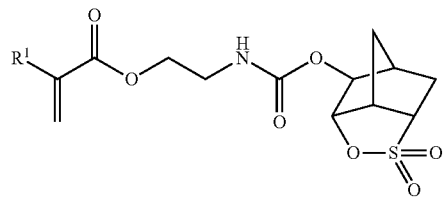
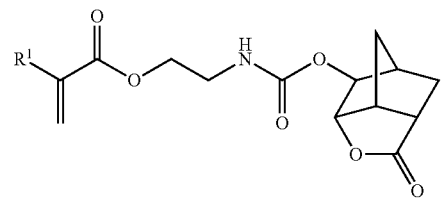
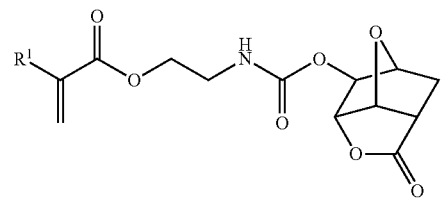

17

-continued

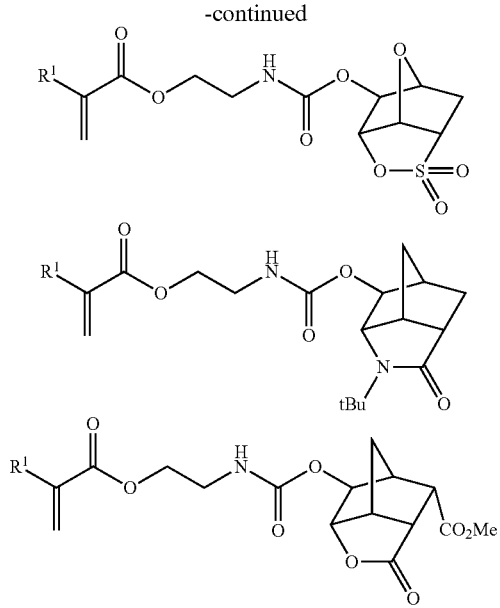

wherein $R^1$ is as defined above, and examples of preferred groups represented by $R^1$ are as described above.

(Production Method for Acrylic Ester Derivative (1))

No particular limitation is imposed on the method for producing the acrylic ester derivative (1) of the present invention, and, for example, the acrylic ester derivative (1) may be produced as described below. Specifically, the acrylic ester derivative (1) may be produced by causing an isocyanate derivative (hereinafter may be referred to as "isocyanate derivative (2)") to be react with an alcohol derivative (hereinafter may be referred to as "alcohol derivative (3)") optionally in the presence of a catalyst, a polymerization inhibitor, a solvent, etc. Hereinafter, this reaction may be referred to as "reaction (a)."

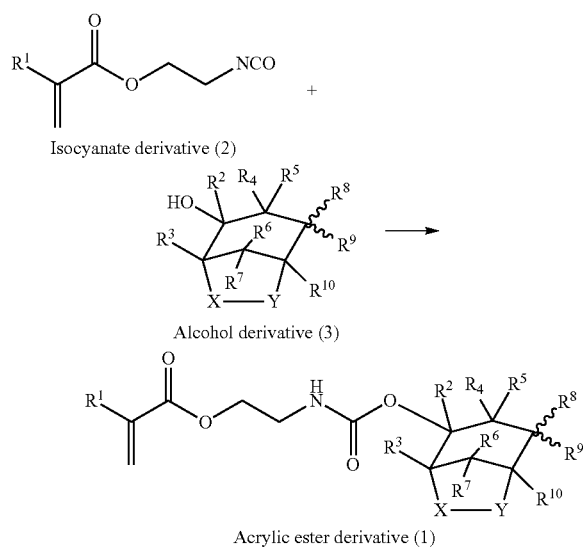

(In the Formula, $R^1$ to $R^{10}$, X, Y, and the Wavy Lines are as Defined Above.)

Reaction (a) will next be described in detail.

Examples of the isocyanate derivative (2) include 2-acryloyloxyethyl isocyanate, 2-methacryloyloxyethyl isocyanate, and 2-(2-trifluoromethylacryloyloxy)ethyl isocyanate. Of these, 2-acryloyloxyethyl isocyanate and 2-methacryloyloxyethyl isocyanate are preferred, from the viewpoint of easy availability.

The amount of the isocyanate derivative (2) employed is preferably 0.8 to 5 mol on the basis of 1 mol of the alcohol derivative (3). From the viewpoints of economy and easy post-treatment, the amount is more preferably 1 to 3 mol.

No particular limitation is imposed on the method for obtaining an alcohol derivative (3). Some alcohol derivatives (3) may be industrially available. Alternatively, an alcohol derivative of interest may be produced through the following procedure: the corresponding diene and dienophile are subjected to Diels-Alder reaction to thereby form an adduct, and the adduct is subjected to epoxidation reaction, optionally after formation of an intermediate from the adduct. Alternatively, an alcohol derivative of interest may be produced by, for example, forming an epoxy compound through epoxidation reaction, and then treating the epoxy compound with, for example, a basic substance.

For example, an alcohol derivative (3) in which each of $R^2$, $R^3$, $R^6$, $R^7$, $R^8$, $R^9$, and $R^{10}$ is a hydrogen atom, $R^4$ and $R^6$ are linked together to form a methylene group, X is —O—, and Y is $>S(=O)_2$; i.e., 5-hydroxy-2,6-norbornane sultone, may be produced through the following procedure. Specifically, cyclopentadiene and vinylsulfonyl chloride generated in the reaction system are subjected to Diels-Alder reaction, to thereby produce 5-norbornene-2-sulfonyl chloride; subsequently, the 5-norbornene-2-sulfonyl chloride is brought into contact with an aqueous sodium hydroxide solution, to thereby produce 5-norbornene-2-sulfonic acid sodium salt; and the salt is subjected to epoxidation reaction with performic acid, to thereby produce the product of interest (see Japanese Patent Application Laid-Open ( ) No. 2010-83873).

Alternatively, an alcohol derivative (3) in which each of $R^2$, $R^3$, $R^8$, $R^7$, $R^8$, $R^9$, and $R^{10}$ is a hydrogen atom, $R^4$ and $R^6$ are linked together to form a methylene group, X is $>N—R^{12}$ wherein $R^{12}$ is a t-butyl group, and Y is $>C=O$ may be produced through the following procedure. Specifically, cyclopentadiene and acryloyl chloride are subjected to Diels-Alder reaction, and the resultant product is caused to react with t-butylamine, to thereby produce N-t-butylbicyclo[2.2.1]hept-5-ene-2-carboxamide. The N-t-butylbicyclo[2.2.1]hept-5-ene-2-carboxamide is subjected to epoxidation reaction by bringing it into contact with m-chloroperbenzoic acid in the presence of a basic compound such as potassium carbonate, to thereby produce N-t-butyl-5,6-epoxybicyclo[2.2.1]hepta-2-carboxamide. The epoxy compound is caused to react with a basic compound such as potassium t-butoxide, to thereby produce the product of interest.

Alternatively, an alcohol derivative (3) in which each of $R^2$, $R^3$, $R^5$, $R^7$, $R^8$, $R^9$, and $R^{10}$ is a hydrogen atom, $R^4$ and $R^6$ are linked together to form a methylene group, X is —O—, and Y is $>C=O$ may be produced through the method disclosed in "J. Chem. Soc., H. B. Henbest, p. 221-226 (1959)."

Another alcohol derivative (3) may be produced according to, for example, any of the aforementioned methods, a known method, or any method described in the Examples of this specification.

Reaction (a) may be carried out in the presence or absence of a catalyst. Examples of the catalyst include mineral acids such as hydrochloric acid and sulfuric acid; Lewis acids such as boron trifluoride, aluminum trichloride, and dibutyltin dilaurate; tertiary amines such as triethylamine, tributylamine, N,N-dimethylaniline, 1,4-diazabicyclo[2.2.2]octane, 1,5-diazabicyclo[4.3.0]non-5-ene, and 1,8-diazabicyclo

[5.4.0]undec-7-ene; and nitrogen-containing heterocyclic aromatic compounds such as pyridine, 2-methylpyridine, and 4-(dimethylamino)pyridine.

Reaction (a) is preferably carried out in the presence of a catalyst, from the viewpoint of reaction rate. A single catalyst may be employed, or two or more catalysts may be employed in combination, so long as an acid is not mixed with a base.

When reaction (a) is carried out in the presence of a catalyst, the amount of the catalyst employed is preferably 0.001 to 0.5 mol, more preferably 0.005 to 0.2 mol, on the basis of 1 mol of the alcohol derivative (3).

Reaction (a) may be carried out in the presence or absence of a polymerization inhibitor. No particular limitation is imposed on the polymerization inhibitor employed. Examples of the polymerization inhibitor include quinone compounds such as hydroquinone, methoxyphenol, benzoquinone, toluquinone, and p-t-butylcatechol; alkylphenol compounds such as 2,6-di-t-butylphenol, 2,4-di-t-butylphenol, and 2-t-butyl-4,6-dimethylphenol; amine compounds such as phenothiazine; and 2,2,6,6-tetramethylpiperidine-N-oxyl compounds such as 2,2,6,6-tetramethylpiperidine-N-oxyl and 4-acetamido-2,2,6,6-tetramethylpiperidine-N-oxyl. These polymerization inhibitors may be employed singly or in combination of two or more species.

When a polymerization inhibitor is employed, the amount of the polymerization inhibitor is preferably 0.001 to 5 mass %, more preferably 0.001 to 1 mass %, much more preferably 0.005 to 0.5 mass %, on the basis of the mass of the entire reaction mixture, exclusive of the below-described solvent(s).

Reaction (a) may be carried out in the presence or absence of a solvent. No particular limitation is imposed on the solvent employed, so long as it does not inhibit the reaction. Examples of the solvent include saturated hydrocarbons such as hexane, heptane, octane, and cyclohexane; aromatic hydrocarbons such as benzene, toluene, and xylene; chlorinated hydrocarbons such as methylene chloride, 1,2-dichloroethane, and chloroform; halogenated aromatic hydrocarbons such as chlorobenzene and fluorobenzene; ethers such as diethyl ether, diisopropyl ether, tetrahydrofuran, 1,4-dioxane, cyclopentyl methyl ether, and 1,2-dimethoxyethane; esters such as methyl acetate, ethyl acetate, and propyl acetate; nitriles such as acetonitrile, propionitrile, and benzonitrile; and amides such as N,N-dimethylformamide, N,N-dimethylacetamide, and N-methylpyrrolidone. These solvents may be employed singly or in combination of two or more species.

When reaction (a) is carried out in the presence of a solvent, the amount of the solvent employed is preferably 0.5 to 100 parts by mass on the basis of 1 part by mass of the alcohol derivative (3). In order to facilitate post-treatment, the amount is more preferably 0.5 to 20 parts by mass.

The reaction temperature may vary with, for example, the isocyanate derivative (2) and alcohol derivative (3) employed, or the type of an optionally employed catalyst or solvent. The reaction temperature is preferably about −30 to about 100° C., more preferably −10 to 80° C.

No particular limitation is imposed on the reaction pressure, but the reaction is preferably carried out at ambient pressure for the sake of convenience.

The reaction time may vary with, for example, the isocyanate derivative (2) and alcohol derivative (3) employed, or the type of an optionally employed catalyst or solvent. The reaction time is preferably about 0.5 hours to about 48 hours, more preferably 1 hour to 24 hours.

Reaction (a) is preferably carried out in an atmosphere of an inert gas such as nitrogen or argon, from the viewpoint of safety.

No particular limitation is imposed on the method for carrying out reaction (a). Also, no particular limitation is imposed on the method and order of addition of reagents, and the reagents may be added through any method in any order.

Reaction (a) is preferably carried out through a method in which an alcohol derivative (3), and optionally a catalyst and a solvent are added to a batch-type reactor, and an isocyanate derivative (2) is added to the resultant mixture at a specific reaction temperature under a specific reaction pressure.

Separation and purification of an acrylic ester derivative (1) from the reaction mixture obtained by the aforementioned method may be carried out through a method which is generally employed for separation and purification of an organic compound.

For example, separation of an acrylic ester derivative (1) may be carried out by adding water to the reaction mixture after completion of reaction, subjecting the mixture to extraction with an organic solvent, and concentrating the resultant organic layer. Optionally, purification may be carried out through, for example, recrystallization, distillation, or silica gel chromatography, to thereby produce an acrylic ester derivative (1) of higher purity.

Optionally, the metal content of the thus-produced acrylic ester derivative (1) may be reduced by adding a chelating agent such as nitrilotriacetic acid or ethylenediaminetetraacetic acid to the derivative, and subjecting the resultant mixture to filtration, or treatment by means of a metal removal filter such as "ZETA PLUS (registered trademark)" (trade name, product of Sumitomo 3M Limited), PROTEGO (trade name, product of Nihon Entegris K.K.), or ION CLEAN (trade name, product of Pall Corporation).

[Polymer]

A homopolymer of the acrylic ester derivative (1) of the present invention or a copolymer of the acrylic ester derivative (1) and another polymerizable compound is useful as a polymer for a photoresist composition.

The polymer of the present invention contains a structural unit derived from an acrylic ester derivative (1) in an amount of more than 0 mol % to 100 mol %. The amount of the structural unit is preferably 10 to 80 mol %, more preferably 20 to 70 mol %, much more preferably 30 to 70 mol %, for improvement of LWR and resolution.

Specific examples of the polymerizable compound which can be copolymerized with the acrylic ester derivative (1) (hereinafter the compound may be referred to as "copolymerizable monomer") include, but are not particularly limited to, compounds represented by the following chemical formulas.

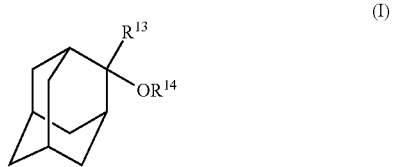

(I)

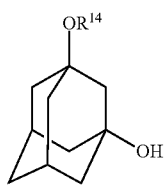
(II)

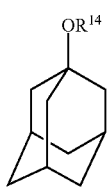
(III)

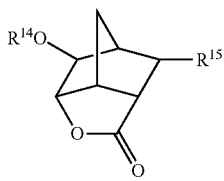
(IV)

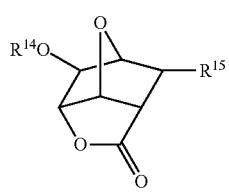
(V)

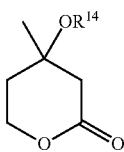
(VI)

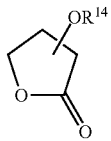
(VII)

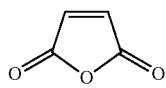
(VIII)

(IX)

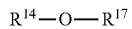
(X)

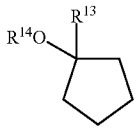
(XI)

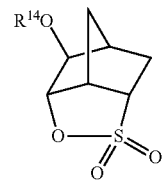
(XII)

In the aforementioned formulas (I) to (XII), $R^{13}$ represents a hydrogen atom or a C1 to C3 alkyl group; $R^{14}$ represents a polymerizable group; $R^{15}$ represents a hydrogen atom or —$COOR^{16}$; $R^{16}$ represents a C1 to C3 alkyl group; and $R^{17}$ represents a C1 to C4 alkyl group.

Examples of the C1 to C3 alkyl group represented by each of $R^{13}$ and $R^{16}$ in the copolymerizable monomer include methyl, ethyl, n-propyl, and isopropyl. Examples of the alkyl group represented by $R^{17}$ include methyl, ethyl, n-propyl, isopropyl, n-butyl, isobutyl, s-butyl, and t-butyl. Examples of the polymerizable group represented by $R^{14}$ include acryloyl, methacryloyl, vinyl, and crotonoyl.

Among the aforementioned copolymerizable monomers, preferred are copolymerizable monomers represented by formulas (I), (II), (IV), (V), (VI), (VII), (XI), and (XII). More preferably, a copolymerizable monomer represented by formula (I) is employed in combination with a copolymerizable monomer represented by formula (II).

(Production Method for Polymer)

The polymer may be produced through radical polymerization by a customary method. Particularly, a polymer having a small molecular weight distribution is synthesized through, for example, living radical polymerization.

In a general radical polymerization method, optionally one or more acrylic ester derivatives (1) and optionally one or more of the aforementioned copolymerizable monomers are polymerized in the presence of a radical polymerization initiator, a solvent, and optionally a chain transfer agent.

No particular limitation is imposed on the method for carrying out radical polymerization, and radical polymerization may be carried out through a conventional method employed for production of an acrylic resin, such as solution polymerization, emulsion polymerization, suspension polymerization, or bulk polymerization.

Examples of the aforementioned radical polymerization initiator include hydroperoxide compounds such as t-butyl hydroperoxide and cumene hydroperoxide; dialkyl peroxide compounds such as di-t-butyl peroxide, t-butyl-α-cumyl peroxide, and di-α-cumyl peroxide; diacyl peroxide compounds such as benzoyl peroxide and diisobutyryl peroxide; and azo compounds such as 2,2'-azobisisobutyronitrile and dimethyl 2,2'-azobisisobutyrate.

The amount of the radical polymerization initiator employed may be appropriately determined in consideration of polymerization conditions, including the type and amount of acrylic ester derivative (1), copolymerizable monomer, chain transfer agent, and solvent employed for polymerization reaction, and polymerization temperature. Generally, the amount of the radical polymerization initiator is preferably 0.005 to 0.2 mol, more preferably 0.01 to 0.15 mol, on the basis of 1 mol of all the polymerizable compounds [corresponding to the total amount of an acrylic ester derivative (1) and a copolymerizable monomer, the same shall apply hereinafter].

Examples of the aforementioned chain transfer agent include thiol compounds such as dodecanethiol, mercaptoethanol, mercaptopropanol, mercaptoacetic acid, and mercaptopropionic acid. When a chain transfer agent is employed, generally, the amount thereof is preferably 0.005 to 0.2 mol, more preferably 0.01 to 0.15 mol, on the basis of 1 mol of all the polymerizable compounds.

No particular limitation is imposed on the aforementioned solvent, so long as it does not inhibit polymerization reaction. Examples of the solvent include glycol ethers such as propylene glycol monoethyl ether, propylene glycol monomethyl ether acetate, ethylene glycol monomethyl ether, ethylene glycol monomethyl ether acetate, ethylene glycol monomethyl ether propionate, ethylene glycol monobutyl ether, ethylene glycol monobutyl ether acetate, and diethylene glycol dimethyl ether; esters such as ethyl lactate, methyl 3-methoxypropionate, methyl acetate, ethyl acetate, and propyl acetate; ketones such as acetone, methyl ethyl ketone, methyl isopropyl ketone, methyl isobutyl ketone, methyl amyl ketone, cyclopentanone, and cyclohexanone; and ethers such as diethyl ether, diisopropyl ether, dibutyl ether, tetrahydrofuran, and 1,4-dioxane.

Generally, the amount of the solvent employed is preferably 0.5 to 20 parts by mass on the basis of 1 part by mass of all the polymerizable compounds. From the viewpoint of economy, the amount is more preferably 1 to 10 parts by mass.

Generally, the polymerization temperature is preferably 40 to 150° C. The polymerization temperature is more preferably 60 to 120° C., from the viewpoint of the stability of a polymer produced.

The polymerization reaction time may vary with polymerization conditions, including the type and amount of acrylic ester derivative (1), copolymerizable monomer, polymerization initiator, and solvent employed, and polymerization reaction temperature. Generally, the polymerization time is preferably 30 minutes to 48 hours, more preferably 1 hour to 24 hours.

Polymerization reaction is preferably carried out in an atmosphere of an inert gas such as nitrogen or argon.

The thus-produced polymer may be isolated through a common process such as reprecipitation. The thus-isolated polymer may be dried through, for example, vacuum drying.

Examples of the solvent employed for the reprecipitation process include aliphatic hydrocarbons such as pentane and hexane; alicyclic hydrocarbons such as cyclohexane; aromatic hydrocarbons such as benzene and xylene; halogenated hydrocarbons such as methylene chloride, chloroform, chlorobenzene, and dichlorobenzene; nitrated hydrocarbons such as nitromethane; nitriles such as acetonitrile and benzonitrile; ethers such as diethyl ether, diisopropyl ether, tetrahydrofuran, and 1,4-dioxane; ketones such as acetone and methyl ethyl ketone; carboxylic acids such as acetic acid; esters such as ethyl acetate and butyl acetate; carbonates such as dimethyl carbonate, diethyl carbonate, and ethylene carbonate; alcohols such as methanol, ethanol, propanol, isopropyl alcohol, and butanol; and water. These solvents may be employed singly or in combination of two or more species.

The amount of the solvent employed for the reprecipitation process may vary with the type of the polymer or solvent. Generally, the amount of the solvent is preferably 0.5 to 100 parts by mass on the basis of 1 part by mass of the polymer. From the viewpoint of economy, the amount is more preferably 1 to 50 parts by mass.

No particular limitation is imposed on the weight average molecular weight (Mw) of the polymer, but the Mw is preferably 500 to 50,000, more preferably 1,000 to 30,000, much more preferably 5,000 to 15,000. When the Mw falls within the above preferred range, the polymer is highly useful as a component of the below-described photoresist composition. The Mw of the polymer is determined through the method described hereinbelow in the Examples.

The molecular weight distribution (Mw/Mn) of the polymer is preferably 3 or less, more preferably 2.5 or less, much more preferably 2 or less, for improvement of LWR and resolution.

[Photoresist Composition]

The photoresist composition of the present invention is prepared by mixing the aforementioned polymer with a photoacid generator and a solvent, and optionally a basic compound, a surfactant, and an additional additive. The respective components will next be described.

(Photoacid Generator)

No particular limitation is imposed on the photoacid generator employed, and the photoacid generator may be any known photoacid generator which is generally employed in conventional chemically amplified resists. Examples of the photoacid generator include onium salt photoacid generators such as iodonium salts and sulfonium salts; oxime sulfonate photoacid generators; bisalkyl or bisarylsulfonyldiazomethane photoacid generators; nitrobenzyl sulfonate photoacid generators; iminosulfonate photoacid generators; and disulfone photoacid generators. These photoacid generators may be employed singly or in combination of two or more species. Of these, an onium salt photoacid generator is preferred. More preferred is a fluorine-containing onium salt containing a fluorine-containing alkyl sulfonate ion as an anion, since such an onium salt generates a strong acid.

Specific examples of the aforementioned fluorine-containing onium salt include diphenyliodonium trifluoromethanesulfonate or nonafluorobutanesulfonate; bis(4-tert-butylphenyl)iodonium trifluoromethanesulfonate or nonafluorobutanesulfonate; triphenylsulfonium trifluoromethanesulfonate, heptafluoropropanesulfonate, or nonafluorobutanesulfonate; tri(4-methylphenyl)sulfonium trifluoromethanesulfonate, heptafluoropropanesulfonate, or nonafluorobutanesulfonate; dimethyl(4-hydroxynaphthyl)sulfonium trifluoromethanesulfonate, heptafluoropropanesulfonate, or nonafluorobutanesulfonate; monophenyldimethylsulfonium trifluoromethanesulfonate, heptafluoropropanesulfonate, or nonafluorobutanesulfonate; diphenylmonomethylsulfonium trifluoromethanesulfonate, heptafluoropropanesulfonate, or nonafluorobutanesulfonate; (4-methylphenyl)diphenylsulfonium trifluoromethanesulfonate, heptafluoropropanesulfonate, or nonafluorobutanesulfonate; (4-methoxyphenyl)diphenylsulfonium trifluoromethanesulfonate, heptafluoropropanesulfonate, or nonafluorobutanesulfonate; and tri(4-tert-butyl)phenylsulfonium trifluoromethanesulfonate, heptafluoropropanesulfonate, or nonafluorobutanesulfonate. These onium salts may be employed singly or in combination of two or more species.

Generally, the amount of the photoacid generator incorporated is preferably 0.1 to 30 parts by mass, more preferably 0.5 to 10 parts by mass, on the basis of 100 parts by mass of the aforementioned polymer, in order to secure the sensitivity and developability of the photoresist composition.

(Solvent)

Examples of the solvent incorporated into the photoresist composition include glycol ethers such as propylene glycol monoethyl ether, propylene glycol monomethyl ether acetate, ethylene glycol monomethyl ether, ethylene glycol monomethyl ether acetate, ethylene glycol monomethyl ether propionate, ethylene glycol monobutyl ether, ethylene glycol monobutyl ether acetate, and diethylene glycol dimethyl ether; esters such as ethyl lactate, methyl 3-methoxypropionate, methyl acetate, ethyl acetate, and propyl acetate; ketones such as acetone, methyl ethyl ketone, methyl isopropyl ketone, methyl isobutyl ketone, methyl amyl ketone, cyclopentanone, and cyclohexanone; and ethers such as diethyl ether, diisopropyl ether, dibutyl ether, tetrahydrofuran, and 1,4-dioxane. These solvents may be employed singly or in combination of two or more species.

Generally, the amount of the solvent incorporated is preferably 1 to 50 parts by mass, more preferably 2 to 25 parts by mass, on the basis of 1 part by mass of the polymer.

(Basic Compound)

In order to reduce the diffusion rate of an acid in a photoresist film for improvement of resolution, the photoresist composition may optionally contain a basic compound in such an amount that the compound does not impair the properties of the photoresist composition. Examples of the basic compound include amides such as formamide, N-methylformamide, N,N-dimethylformamide, acetamide, N-methylacetamide, N,N-dimethylacetamide, N-(1-adamantyl)acetamide, benzamide, N-acetylethanolamine, 1-acetyl-3-methylpiperidine, pyrrolidone, N-methylpyrrolidone, ε-caprolactam, δ-valerolactam, 2-pyrrolidinone, acrylamide, methacrylamide, t-butylacrylamide, methylenebisacrylamide, methylenebismethacrylamide, N-methylolacrylamide, N-methoxyacrylamide, and diacetoneacrylamide; and amines such as pyridine, 2-methylpyridine, 4-methylpyridine, nicotine, quinoline, acridine, imidazole, 4-methylimidazole, benzimidazole, pyradine, pyrazole, pyrrolidine, N-t-butoxycarbonylpyrrolidine, piperidine, tetrazole, morpholine, 4-methylmorpholine, piperazine, 1,4-diazabicyclo[2.2.2]octane, tributylamine, tripentylamine, trihexylamine, triheptylamine, trioctylamine, and triethanolamine. These basic compounds may be employed singly or in combination of two or more species.

When a basic compound is incorporated, generally, the amount thereof—which may vary with the type of the basic compound—is preferably 0.01 to 10 mol, more preferably 0.05 to 1 mol, on the basis of 1 mol of the photoacid generator.

(Surfactant)

For improvement of coating properties, the photoresist composition may optionally contain a surfactant in such an amount that the surfactant does not impair the properties of the photoresist composition.

Examples of the surfactant include polyoxyethylene lauryl ether, polyoxyethylene stearyl ether, polyoxyethylene oleyl ether, and polyoxyethylene n-octyl phenyl ether. These surfactants may be employed singly or in combination of two or more species.

When a surfactant is incorporated, generally, the amount thereof is preferably 2 parts by mass or less on the basis of 100 parts by mass of the polymer.

(Additional Additive)

The photoresist composition may also contain an additional additive such as a sensitizer, a halation-preventing agent, a shape-improving agent, a storage stabilizer, or an antifoaming agent in such an amount that the additive does not impair the properties of the photoresist composition.

(Photoresist Pattern Formation Method)

A specific resist pattern may be formed through the following procedure: the photoresist composition is coated onto a substrate; the composition-coated substrate is generally pre-baked at preferably 70 to 160° C. for 1 to 10 minutes; the resultant product is irradiated with a radiation (exposed to light) via a specific mask; subsequently, post-exposure baking is carried out at preferably 70 to 160° C. for 1 to 5 minutes, to thereby form a latent image pattern; and then development is carried out by use of a developer.

Light exposure may be carried out by means of a radiation of any wavelength; for example, UV rays or X-rays. For the case of a semiconductor resist, g-ray, i-ray, or an excimer laser such as XeCl, KrF, KrCl, ArF, or ArCl is generally employed. Of these, ArF excimer laser is preferably employed, for improvement of micropatterning.

The amount of exposure light is preferably 0.1 to 1,000 mJ/cm$^2$, more preferably 1 to 500 mJ/cm$^2$.

Examples of the developer include alkaline aqueous solutions prepared by dissolving, in water, inorganic bases such as sodium hydroxide, potassium hydroxide, sodium carbonate, and aqueous ammonia; alkylamines such as ethylamine, diethylamine, and triethylamine; alcoholamines such as dimethylethanolamine and triethanolamine; and quaternary ammonium salts such as tetramethylammonium hydroxide and tetraethylammonium hydroxide. Of these, an alkaline aqueous solution prepared by dissolving, in water, a quaternary ammonium salt such as tetramethylammonium hydroxide or tetraethylammonium hydroxide is preferably employed.

Generally, the developer concentration is 0.1 to 20 mass, more preferably 0.1 to 10 mass.

EXAMPLES

The present invention will next be described in detail by way of Examples, which should not be construed as limiting the invention thereto. Measurement of Mw and Mn and calculation of molecular weight distribution were carried out as described below.

(Measurement of Mw and Mn, and Calculation of Molecular Weight Distribution)

For measurement of weight average molecular weight (Mw) and number average molecular weight (Mn), gel permeation chromatography (GPC) employing a differential refractometer as a detector and tetrahydrofuran (THF) as an eluent was carried out under the below-described conditions, and a calibration curve prepared by use of standard polystyrene was employed for molecular weight conversion. Molecular weight distribution (Mw/Mn) was determined by dividing weight average molecular weight (Mw) by number average molecular weight (Mn).

By means of a column prepared by connecting "TSK-gel SUPER HZM-H" (trade name, product of Tosoh Corporation, 4.6 mm×150 mm)×2 and "TSK-gel SUPER HZ2000" (trade name, product of Tosoh Corporation, 4.6 mm×150 mm)×1 in series, GPC measurement was carried out under the following conditions: column temperature: 40° C., differential refractometer temperature: 40° C., and eluent flow rate: 0.35 mL/minute.

Synthesis Example 1

Synthesis of 5-hydroxy-2,6-norbornane sultone

To a four-necked flask having a capacity of 1 L and equipped with a stirrer and a thermometer, 0.40 g of phenothiazine, 1154.0 g of tetrahydrofuran, and 87.0 g (1.32 mol) of cyclopentadiene were added, and the resultant mixture was cooled to 5° C. or lower under stirring. Subsequently, 195.7 g (1.20 mol) of 2-chloroethanesulfonyl chloride and 146.0 g (1.45 mol) of triethylamine were respectively added to separate dropping funnels, and they were simultaneously added dropwise to the flask at an internal temperature of 5 to 10° C. over 3 hours.

After completion of the addition, the resultant reaction mixture was stirred at 5 to 10° C. for 3 hours, and then the thus-precipitated salt was separated through filtration under reduced pressure, followed by addition of 600.0 g of THF to the salt separated through filtration, to thereby obtain 1632.8 g of a filtrate (hereinafter the filtrate will be referred to as "filtrate (A)"). The filtrate (A) was analyzed through gas chromatography. As a result, the filtrate was found to contain 178.2 g (0.925 mol) of 5-norbornene-2-sulfonyl chloride (yield with respect to 2-chloroethanesulfonyl chloride: 77.1%).

To a three-necked flask having a capacity of 3 L and equipped with a stirrer and a thermometer, 920 g of water was added and the flask was cooled to 20° C. or lower. Under stirring, 80.30 g (2.01 mol) of sodium hydroxide was added to the flask so that the internal temperature was maintained at 20° C. or lower. 1300 g Of "filtrate (A)" (5-norbornene-2-sulfonyl chloride: 141.9 g, 0.737 mol) was added dropwise to the flask at an internal temperature of 20 to 25° C. over 4 hours.

One hour after completion of the addition, the resultant reaction mixture was analyzed through gas chromatography. As a result, 5-norbornene-2-sulfonyl chloride was found to completely disappear. The reaction mixture was concentrated under reduced pressure, to thereby remove THF. Thereafter, the resultant concentrate was transferred to a 2 L separating funnel and washed thrice with 300 g of toluene, to thereby obtain 1065.3 g of an aqueous solution containing 5-norbornene-2-sulfonic acid sodium salt (hereinafter the aqueous solution will be referred to as "aqueous solution (A)").

"Aqueous solution (A)" was completely added to a three-necked flask having a capacity of 3 L and equipped with a stirrer and a thermometer, and the flask was cooled to 10° C. 93.27 g (2.01 mol) of 99% formic acid was added dropwise to the flask at an internal temperature of 11 to 15° C., and then the flask was heated so as to attain an internal temperature of 50 to 53° C. Thereafter, 162.50 g (1.43 mol) of 30% aqueous hydrogen peroxide was added dropwise to the flask over 3 hours. After completion of the addition, the internal temperature was further maintained at 50° C. or thereabout. Seventeen hours after completion of the addition, the resultant reaction mixture was analyzed through HPLC. As a result, the conversion of 5-norbornene-2-sulfonic acid was found to be 98.7%.

After cooling of the reaction mixture to 15° C., 36.55 g (0.29 mol) of sodium sulfite was slowly added to the flask at an internal temperature of 15 to 18° C., and no detection of hydrogen peroxide was confirmed by means of starch paper. Subsequently, 140.95 g (1.68 mol) of sodium hydrogencarbonate was slowly added to the flask at an internal temperature of 15 to 17° C., to thereby adjust the pH of the reaction mixture to 7.3. The reaction mixture was subjected to extraction twice with 900 g of ethyl acetate, and the resultant organic layers were combined and concentrated under reduced pressure, to thereby obtain 69.15 g of a yellow-white solid. After dissolution of this solid in 140 g of ethyl acetate at 50° C., the resultant solution was slowly cooled to 10° C., and the thus-precipitated crystals were separated through filtration. The crystals separated through filtration were washed with 30 g of ethyl acetate at 5° C., and then dried under reduced pressure at 40° C. for 2 hours, to thereby obtain 53.9 g (purity: 99.1%, 0.28 mol) of 5-hydroxy-2,6-norbornane sultone (yield with respect to 5-norbornene-2-sulfonyl chloride: 38.1%).

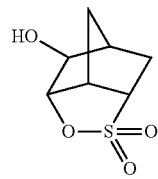

Example 1

Synthesis of 2,6-norbornane sulton-5-yl(2-methacryloyloxyethyl)carbamate

To a four-necked flask having a capacity of 1 L and equipped with a thermometer, a stirrer, a nitrogen conduit, and a dropping funnel, 100.0 g (525.7 mmol) of 5-hydroxy-2,6-norbornane sultone obtained in Synthesis Example 1, 50 mg of 4-acetamido-2,2,6,6-tetramethylpiperidine-N-oxyl, 600 g of ethyl acetate, and 4.00 g (26.3 mmol) of 1,8-diazabicyclo[5.4.0]undec-7-ene were added, and 89.7 g (578.4 mmol) of 2-methacryloyloxyethyl isocyanate was added dropwise to the flask at an internal temperature of 24 to 27° C. over about 2 hours. After completion of the addition, the resultant mixture was stirred at 25° C. for one hour. Thereafter, the resultant reaction mixture was analyzed by means of a high-performance liquid chromatography (HPLC) apparatus having an RI detector. As a result, 5-hydroxy-2,6-norbornane sultone was found to completely disappear.

155.4 g Of 0.5 mass % aqueous hydrochloric acid was added dropwise to the resultant reaction mixture at an internal temperature of 25 to 30° C. After completion of the addition, the mixture was heated to 40° C. and allowed to stand for 30 minutes. The thus-separated aqueous layer (lower layer) was removed, and then the organic layer (upper layer) was washed five times with 300 g of ion-exchange water. In this washing operation, the liquid mixture was allowed to stand at an internal temperature of 45° C. for liquid-liquid separation. 16 mg Of p-methoxyphenol and 16 mg of phenothiazine were added to the organic layer, and the resultant mixture was concentrated under reduced pressure, to thereby obtain 211.2 g of a concentrate. 246.3 g Of ethyl acetate was added to the concentrate, and the resultant mixture was heated to 55° C. Subsequently, the mixture was cooled to −10° C., and then the thus-precipitated crystals were separated through filtration. The resultant wet crystals were dried under reduced pressure, to thereby obtain 128.1 g (white solid, 371.3 mmol, yield: 70.6%) of 2,6-norbornane sulton-5-yl(2-methacryloyloxyethyl)carbamate.

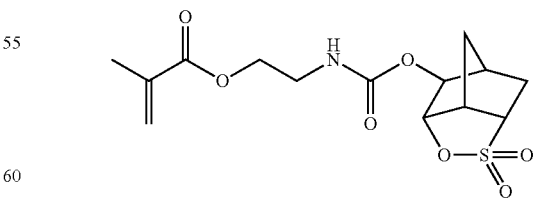

$^1$H-NMR (400 MHz, CDCl$_3$, TMS, ppm) δ: 6.12 (1H, s), 5.61 (1H, m), 4.99 (1H, br), 4.71 (1H, d, J=4.4 Hz), 4.67 (1H, s), 4.24 (2H, t, J=5.2 Hz), 3.4-3.6 (4H, m), 2.59 (1H, br), 2.12-2.16 (2H, m), 2.05 (1H, d, J=12.0 Hz), 1.95 (3H, s), 1.75 (1H, d, J=12.0 Hz)

Synthesis Example 2

Synthesis of 5-hydroxy-2,6-norbornane carbolactone

To a four-necked flask having a capacity of 1 L and equipped with a stirrer, a thermometer, and a dropping funnel, 0.40 g of p-methoxyphenol, 108.1 g (1.50 mol) of acrylic acid, and 300 mL of toluene were added, and 109.1 g (1.65 mol) of cyclopentadiene was added dropwise to the flask from the dropping funnel at 40° C. or lower over 2 hours. After completion of the addition, the resultant mixture was stirred at room temperature for 10 hours, and then concentrated under reduced pressure, to thereby obtain 167.3 g (1.21 mol) of 5-norbornene-2-carboxylic acid.

The entire amount of the above-obtained 5-norbornene-2-carboxylic acid was mixed with 94.6 g (1.81 mol) of 88% formic acid at 20 to 30° C. in a four-necked flask having a capacity of 1 L and equipped with a stirrer, a thermometer, and a dropping funnel, and then the resultant mixture was heated so as to attain an internal temperature of 48 to 50° C. Subsequently, 162.5 g (1.43 mol) of 30% aqueous hydrogen peroxide was added dropwise to the flask over 6 hours. After completion of the addition, the resultant mixture was further stirred at an internal temperature of 50° C. or thereabout for 10 hours. After cooling of the resultant reaction mixture to 15° C., 30.5 g of sodium sulfite was added to the flask at an internal temperature of 15 to 20° C., and no detection of hydrogen peroxide was confirmed by means of starch paper. Thereafter, the pH of the reaction mixture was adjusted to 7.5 with 20% aqueous sodium hydroxide solution. The reaction mixture was subjected to extraction thrice with 400 g of ethyl acetate, and the resultant organic layers were mixed together and concentrated under reduced pressure. 150 g Of ethyl acetate and 750 g of toluene were added to the resultant solid, and the resultant mixture was heated. After complete dissolution of the solid, the mixture was slowly cooled to 0° C., and the thus-precipitated crystals were separated through filtration. The crystals separated through filtration were washed with 200 g of toluene at 5° C., and then dried under reduced pressure at 40° C. for 2 hours, to thereby obtain 117.9 g (purity: 99.3%, 0.76 mol) of 5-hydroxy-2,6-norbornane carbolactone.

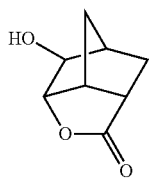

Example 2

Synthesis of 2,6-norbornane carbolacton-5-yl(2-methacryloyloxyethyl)carbamate

To a three-necked flask having a capacity of 100 mL and equipped with a thermometer, a stirrer, and a nitrogen conduit, 5.00 g (32.4 mmol) of 5-hydroxy-2,6-norbornane carbolactone obtained in Synthesis Example 2, 15 mg of 4-acetamido-2,2,6,6-tetramethylpiperidine-N-oxyl, 30 g of ethyl acetate, and 226 mg (1.48 mmol) of 1,8-diazabicyclo[5.4.0]undec-7-ene were added, and 5.51 g (35.5 mmol) of 2-methacryloyloxyethyl isocyanate was added dropwise to the flask at an internal temperature of 24 to 31° C. over about 0.5 hours. After completion of the addition, the resultant mixture was stirred at 25° C. for 3.2 hours. Thereafter, the resultant reaction mixture was analyzed by means of an HPLC apparatus having a UV detector. As a result, the conversion of 5-hydroxy-2,6-norbornane carbolactone was found to be 86.7%.

20.0 g Of water and 1.4 g of 1.0 mass % aqueous hydrochloric acid were sequentially added dropwise to the resultant reaction mixture at an internal temperature of 25 to 30° C. After completion of the addition, the mixture was allowed to stand for 60 minutes. The thus-separated aqueous layer (lower layer) was removed, and then the organic layer (upper layer) was washed four times with 20 g of ion-exchange water. The organic layer was concentrated under reduced pressure, to thereby obtain 10.8 g of a concentrate. The concentrate was subjected to separation/purification through silica gel column chromatography (developing solution: ethyl acetate/methanol=3/1 (by volume)), to thereby obtain 7.78 g (pale yellow liquid, 25.2 mmol, yield: 77.6%) of 2,6-norbornane carbolacton-5-yl(2-methacryloyloxyethyl) carbamate.

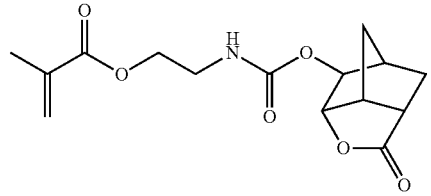 [SMILES: C=C(C)C(=O)OCCNC(=O)OC1C2CC3C(=O)OC1C3C2]

$^1$H-NMR (400 MHz, CDCl$_3$, TMS, ppm) δ: 6.12 (1H, m), 5.61 (1H, m), 4.96 (1H, br), 4.53 (2H, m), 4.25 (2H, t, J=5.2 Hz), 3.50 (2H, dt, J=5.2, 5.2 Hz), 3.17 (1H, br), 2.50-2.60 (2H, m), 1.95-1.99 (4H, m), 1.75 (1H, d, J=13.6 Hz), 1.59-1.62 (2H, m)

Synthesis Example 3

Synthesis of 5-hydroxy-2,6-(7-oxanorbornane)carbolactone

To a four-necked flask having a capacity of 100 mL and equipped with a stirrer and a thermometer, 48.0 g (0.705 mol) of furan and 20.0 g (0.232 mol) of methyl acrylate were added, and the resultant mixture was cooled to −20° C. 3.0 mL Of boron trifluoride-diethyl ether complex was added dropwise to the flask while the internal temperature was maintained at −15 to −18° C. After completion of the addition, the resultant mixture was continuously stirred at an internal temperature of 0 to 5° C. for 14 hours. The resultant reaction mixture was concentrated under reduced pressure, and the resultant concentrate was dissolved in 300 g of ethyl acetate. The resultant solution was sequentially washed with 50 g of water, 50 g of saturated aqueous sodium hydrogencarbonate solution, and 50 g of saturated brine, and then concentrated under reduced pressure, to thereby obtain 28.3 g of an oily product.

93.6 g (0.234 mol) Of 10% aqueous sodium hydroxide solution was added to the oily product, and the resultant mixture was stirred at room temperature for 24 hours. Thereafter, the pH of the mixture was adjusted to 2.0 with concentrated hydrochloric acid. The resultant mixture was subjected to extraction thrice with 300 g of ethyl acetate, and the resultant extract layers were combined and concentrated under reduced pressure, to thereby obtain 21.5 g of a solid.

The entire amount of the above-obtained solid was mixed with 12.0 g (0.232 mol) of 88% formic acid at 20 to 30° C. in a four-necked flask having a capacity of 200 mL and equipped with a stirrer, a thermometer, and a dropping funnel, and then the flask was heated so as to attain an internal temperature of 45 to 46° C. Subsequently, 26.1 g (0.232 mol) of 30% aqueous hydrogen peroxide was added dropwise to the flask over 6 hours. After completion of the addition, the resultant mixture was further stirred at an internal temperature of 45° C. or thereabout for 20 hours. The resultant reaction mixture was cooled to 15° C., and then 9.7 g of sodium sulfite was added to the mixture at an internal temperature of 15 to 20° C. After confirmation of no detection of hydrogen peroxide by means of starch paper, the pH of the reaction mixture was adjusted to 7.8 with 20% aqueous sodium hydroxide solution. The resultant mixture was subjected to extraction thrice with 400 g of ethyl acetate, and the resultant organic layers were combined and concentrated under reduced pressure. 30 g Of ethanol was added to the thus-obtained solid, and the resultant mixture was heated. After complete dissolution of the solid, the mixture was slowly cooled to 0° C., and the thus-precipitated crystals were separated through filtration. The crystals separated through filtration were washed with 10 g of ethanol at 0° C., and then dried under reduced pressure at 40° C. for 2 hours, to thereby obtain 10.8 g (purity: 98.9%, 0.068 mol) of 5-hydroxy-2,6-(7-oxanorbornane) carbolactone.

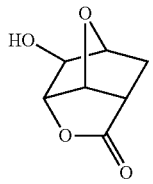

Example 3

Synthesis of 2,6-(7-oxanorbornane)carbolacton-5-yl (2-methacryloyloxyethyl)carbamate To a three-necked flask having a capacity of 50 mL and equipped with a thermometer, a stirrer, and a nitrogen conduit, 1.00 g (6.34 mmol) of 5-hydroxy-2,6-(7-oxanorbornane) carbolactone obtained in Synthesis Example 3, 2.4 mg of 4-acetamido-2,2,6,6-tetramethylpiperidine-N-oxyl, 10.0 g of tetrahydrofuran, 1.00 g (6.34 mmol) of 2-methacryloyloxyethyl isocyanate, and 0.10 g of dibutyltin dilaurate were added, and the resultant mixture was stirred at room temperature for 24 hours. The resultant reaction mixture was analyzed by means of an HPLC apparatus having a UV detector. As a result, the conversion of 5-hydroxy-2,6-(7-oxanorbornane) carbolactone was found to be 93.7%. The reaction mixture was concentrated under reduced pressure, and 4.22 g of the resultant concentrate was cooled at −20° C. overnight.

The thus-precipitated solid was separated through filtration, and the resultant solid was suspended in 19.3 g of hexane, followed by filtration, to thereby obtain 2,6-(7-oxanorbornane) carbolacton-5-yl(2-methacryloyloxyethyl) carbamate (white solid, 1.52 g, 4.88 mmol, yield: 77.0%).

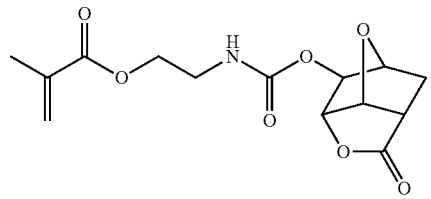 [SMILES: C=C(C)C(=O)OCCNC(=O)OC1C2CC3C(=O)OC1C3O2]

$^1$H-NMR (400 MHz, CDCl$_3$, TMS, ppm) δ: 6.12 (1H, m), 5.61 (1H, m), 5.33 (1H, dd, J=4.8, 4.8 Hz), 5.08 (1H, br), 4.73 (1H, d, J=5.2 Hz), 4.70 (1H, s), 4.64 (1H, d, J=4.8 Hz), 4.24 (2H, t, J=5.2 Hz), 2.74 (1H, ddd, J=11.2, 4.8, 1.2 Hz), 3.51 (2H, dt, J=6.0, 5.2 Hz), 2.25 (1H, ddd, J=13.6, 11.2, 5.6 Hz), 2.07 (1H, dd, J=13.6, 2.0 Hz), 1.95 (3H, s)

Synthesis Example 4

Synthesis of 5-hydroxy-7-oxanorbornane-2,6-sultone

Methyl vinylsulfonate serving as a raw material was synthesized according to the synthesis example described in Angew. Chem., 77(7), 291-302 (1965). Firstly, 326.0 g (2.00 mol) of 2-chloroethanesulfonyl chloride was added to a four-necked flask having a capacity of 2 L and equipped with a stirrer, a thermometer, a dropping funnel and a three-way cock under nitrogen atmosphere, and then cooled in an ice bath. Subsequently, 25 wt % sodium methoxide (methanol solution) was added dropwise to the flask from the dropping funnel so as to attain an internal temperature of 2 to 5° C. After completion of the addition, the ice bath was removed, and the resultant mixture was stirred at room temperature for one hour. The resultant reaction mixture was separated through filtration, and the resultant filtrate was concentrated under reduced pressure. The resultant concentrate was subjected to a simple distillation operation, to thereby obtain 197.2 g (purity: 97.3%, 1.571 mol) of methyl vinylsulfonate (yield with respect to 2-chloroethanesulfonyl chloride: 78.5%).

Subsequently, 5-hydroxy-7-oxanorbornane-2,6-sultone was synthesized according to Example 2 described in Japanese Patent Application Laid-Open ( ) No. 2007-31355.

To a four-necked flask having a capacity of 300 mL and equipped with a stirrer, a dropping funnel, and a thermometer, 150 g (2.20 mol) of furan and 15.0 g of zinc iodide were added, and 41.5 g (0.34 mol) of methyl vinylsulfonate was added to the flask from the dropping funnel at 25 to 27° C. The resultant mixture was continuously stirred at the same temperature for 2 days, and then the resultant reaction mixture was transferred to a 1 L separatory funnel. The reaction mixture was washed twice with 300 mL of water, and then unreacted furan was removed through evaporation under reduced pressure, to thereby obtain 22.0 g of methyl 7-oxabicyclo [2.2.1]hept-2-ene-5-sulfonate.

To a four-necked flask having a capacity of 1000 mL and equipped with a stirrer, a dropping funnel, and a thermometer, 22.0 g of methyl 7-oxabicyclo[2.2.1]hept-2-ene-5-sulfonate and 450 g of methylene chloride were sequentially added, and the resultant mixture was cooled to 4° C. 22.9 g (0.17 mol) of m-chloroperbenzoic acid was slowly added to the flask under stirring so as to attain a temperature of 10° C. or lower. The resultant mixture was stirred at 5 to 7° C. for 4 hours, and then 100 g of saturated aqueous sodium sulfite solution was added to the mixture, followed by stirring for 30 minutes. The mixture was allowed to stand for liquid-liquid separation, and then washing was carried out thrice with 100 g of saturated aqueous sodium hydrogencarbonate solution. The resultant organic layer was concentrated under reduced pressure, to thereby obtain 20.2 g of methyl 2,3-epoxy-7-oxabicyclo[2.2.1]hept-2-ene-5-sulfonate.

To a four-necked flask having a capacity of 300 mL and equipped with a stirrer, a dropping funnel, and a thermometer, 5.0 (mol/L) aqueous sodium hydroxide solution was added, and 29.5 g of methyl 2,3-epoxy-7-oxabicyclo[2.2.1]hept-2-ene-5-sulfonate was added dropwise to the flask from the dropping funnel at an internal temperature of 20 to 23° C. After completion of the addition, the resultant mixture was stirred for 4 hours, and then concentrated hydrochloric acid was added dropwise to the mixture under cooling with ice water, to thereby adjust the pH of the mixture to 7.3. Subsequently, the mixture was subjected to extraction four times with 300 mL of ethyl acetate, and then the resultant organic layers were combined and concentrated. Thereafter, the resultant concentrate was subjected to separation/purification through silica gel column chromatography, to thereby obtain 4.75 g (purity: 98.8%, 0.024 mol) of 5-hydroxy-7-oxanorbornane-2,6-sultone.

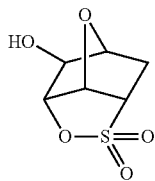

Example 4

Synthesis of 7-oxanorbornane-2,6-sulton-5-yl(2-methacryloyloxyethyl)carbamate

To a three-necked flask having a capacity of 50 mL and equipped with a thermometer, a stirrer, and a nitrogen conduit, 0.30 g (1.56 mmol) of 5-hydroxy-7-oxanorbornane-2,6-sultone obtained in Synthesis Example 4, 1.0 mg of 4-acetamido-2,2,6,6-tetramethylpiperidine-N-oxyl, 1.8 g of ethyl acetate, and 12 mg (0.08 mmol) of 1,8-diazabicyclo[5.4.0]undec-7-ene were added, and 0.27 g (1.74 mmol) of 2-methacryloyloxyethyl isocyanate was added to the flask under stirring at 24 to 26° C., followed by stirring at room temperature for 24 hours. The resultant reaction mixture was analyzed by means of an HPLC apparatus having a UV detector. As a result, the conversion of 5-hydroxy-7-oxanorbornane-2,6-sultone was found to be 100%. 5.0 g Of ethyl acetate was added to the reaction mixture, and the pH of the mixture was adjusted to 3 to 4 with 0.5 wt % aqueous HCl solution. Thereafter, the mixture was separated into an organic layer and an aqueous layer. The organic layer was washed thrice with 2 g of water, and then concentrated under reduced pressure, to thereby obtain 0.54 g of a concentrate. The concentrate was dissolved in 2.0 g of a solvent mixture of ethyl acetate and hexane (ethyl acetate:hexane=2:1 by weight) and then cooled, whereby a white solid was precipitated. The white solid was separated through filtration, to thereby obtain 7-oxanorbornane-2,6-sulton-5-yl(2-methacryloyloxyethyl)carbamate (white solid, 0.22 g, 0.63 mmol, yield: 40.6%).

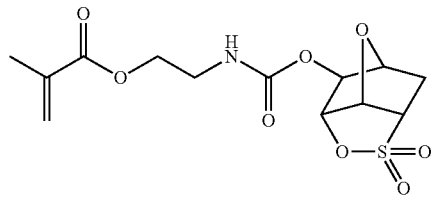 [SMILES: C=C(C)C(=O)OCCNC(=O)OC1C2CC3C(O2)C1OS3(=O)=O]

$^1$H-NMR (400 MHz, CDCl$_3$, TMS, ppm) δ: 6.12 (1H, m), 5.61 (1H, m), 5.52 (1H, dd, J=4.8, 4.8 Hz), 5.12 (1H, br), 4.84 (1H, s), 4.82 (1H, d, J=4.8 Hz), 4.77 (1H, d, J=4.8 Hz), 4.25 (2H, t, J=5.2 Hz), 3.67 (1H, ddd, J=10.0, 4.8, 3.6 Hz), 3.51 (2H, dt, J=5.6, 5.2 Hz), 2.30-2.44 (2H, m), 1.95 (3H, s)

Synthesis Example 5

Synthesis of N-t-butyl-6-hydroxyhexahydro-2-oxo-3,5-methano-4H-cyclopenta[2,3-b]pyrrole To a three-necked flask having a capacity of 2 L and equipped with a thermometer, a stirrer, a nitrogen conduit, 217.2 g (2.400 mol) of acryloyl chloride and 520 g of toluene were added, and then cooled to attain an internal temperature of 0° C. 190.4 g (2.880 mol) of cyclopentadiene was added dropwise to the resultant mixture from the dropping funnel over 1 hour. After completion of the addition, the resultant mixture was stirred at 0° C. for one hour, to thereby prepare a reaction intermediate solution (A).

To a three-necked flask having a capacity of 2 L and equipped with a thermometer, a stirrer, a nitrogen conduit, and a dropping funnel, 201.1 g (2.750 mol) of t-butylamine and 513 g of toluene were added, and then cooled to attain an internal temperature of 0° C. The above-prepared reaction intermediate solution (A) was added dropwise to the resultant mixture from the dropping funnel over 1 hour and 30 minutes, and then the internal temperature was elevated to 25° C. 1800 mL Of ethyl acetate and 300 mL of water were added to the resultant reaction mixture, and the mixture was stirred for 30 minutes and then allowed to stand for liquid-liquid separation, to thereby obtain an organic layer. The organic layer was concentrated under reduced pressure, to thereby obtain a concentrate.

750 mL Of ethyl acetate and 250 mL of hexane were added to the concentrate, and the resultant mixture was heated to 40° C. for dissolution of the concentrate. The mixture was cooled to 2° C. under stirring, and then the thus-precipitated crystals were separated through filtration. The resultant crystals were dried under reduced pressure, to thereby obtain 124.3 g (0.643 mol, yield: 26.8%) of N-t-butylbicyclo[2.2.1]hept-5-ene-2-carboxamide.

To a three-necked flask having a capacity of 2 L and equipped with a thermometer, a stirrer, a nitrogen conduit, and a dropping funnel, 50.0 g (0.259 mol) of N-t-butylbicyclo[2.2.1]hept-5-ene-2-carboxamide, 250 g of methylene chloride, 121.6 g (0.880 mol) of potassium carbonate, and 550 g of water were added, and then the mixture was cooled to attain an internal temperature of 0° C. 75.9 g (0.440 mol) Of m-chloroperbenzoic acid and 1559 g of methylene chloride were added dropwise to the resultant mixture from the dropping funnel over 20 minutes. The mixture was stirred at 0 to 7° C. for 4 hours, and then 22 g of saturated aqueous sodium sulfite solution was added to the mixture, followed by stirring for 30 minutes. The resultant mixture was allowed to stand for liquid-liquid separation, and then the resultant organic layer was washed twice with 400 mL of water. The organic layer was concentrated under reduced pressure, to thereby obtain a concentrate.

554 g Of diisopropyl ether and 222 g of hexane were added to the concentrate, and the internal temperature was elevated to 50° C. for dissolution of the concentrate. Thereafter, the mixture was cooled to 2° C., and the thus-precipitated crystals were separated through filtration. The resultant crystals were dried under reduced pressure, to thereby obtain 26.4 g (0.126 mol, yield: 48.6%) of N-t-butyl-5,6-epoxybicyclo[2.2.1]hepta-2-carboxamide.

To a three-necked flask having a capacity of 2 L and equipped with a thermometer, a stirrer, and a nitrogen conduit, 61.0 g (0.544 mol) of potassium t-butoxide and 1045 g of t-butanol were added, and the resultant mixture was heated to 50° C. 56.9 g (0.272 mol) Of N-t-butyl-5,6-epoxybicyclo[2.2.1]hepta-2-carboxamide was added to the mixture over 1 hour. Subsequently, the internal temperature was lowered to 25° C., and then 620 g of 3.9 mass % hydrochloric acid and 1900 mL of ethyl acetate were added to the flask. The resultant mixture was stirred for 30 minutes, and allowed to stand for liquid-liquid separation. Thereafter, the resultant organic layer was washed twice with 400 mL of water, and the organic layer was concentrated under reduced pressure, to thereby obtain a concentrate.

30 g Of methanol and 820 g of diisopropyl ether were added to the concentrate, and the internal temperature was elevated to 50° C. for dissolution of the concentrate. Subsequently, the resultant mixture was cooled to 0° C., and then the thus-precipitate crude crystals were separated through filtration. 200 g Of ethyl acetate and 200 g of diisopropyl ether were added to the crude crystals, and the internal temperature was elevated to 50° C. for dissolution of the crude crystals. Subsequently, the resultant mixture was cooled to 0° C., and then the thus-precipitate crystals were separated through filtration. The crystals were dried under reduced pressure, to thereby obtain 24.9 g (0.119 mol, yield: 43.8%) of N-t-butyl-6-hydroxyhexahydro-2-oxo-3,5-methano-4H-cyclopenta[2,3-b]pyrrole having the below-described properties.

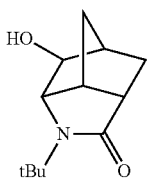

Example 5

Synthesis of N-t-butyl-hexahydro-2-oxo-3,5-methano-4H-cyclopenta[2,3-b]pyrrol-6-yl(2-methacryloyloxyethyl)carbamate To a three-necked flask having a capacity of 100 mL and equipped with a thermometer, a stirrer, and a nitrogen conduit, 5.00 g (23.9 mmol) of N-t-butyl-6-hydroxyhexahydro-2-oxo-3,5-methano-4H-cyclopenta[2,3-b]pyrrole obtained in Synthesis Example 5, 15 mg of 4-acetamido-2,2,6,6-tetramethylpiperidine-N-oxyl, 30.0 g of ethyl acetate, and 0.18 g (1.18 mmol) of 1,8-diazabicyclo[5.4.0]undec-7-ene were added, and 4.13 g (26.6 mmol) of 2-methacryloyloxyethyl isocyanate was added dropwise to the flask under stirring at 24 to 26° C. over 2.4 hours. One hour after completion of the addition, the resultant reaction mixture was analyzed by means of an HPLC apparatus having a UV detector. As a result, the conversion of N-t-butyl-6-hydroxyhexahydro-2-oxo-3,5-methano-4H-cyclopenta[2,3-b]pyrrole was found to be 97%. 20.0 mL Of ethyl acetate was added to the reaction mixture, and the pH of the resultant mixture was adjusted to 3 with 0.5 wt % aqueous HCl solution. Thereafter, the mixture was separated into an organic layer and an aqueous layer. The organic layer was washed five times with 20 g of water, and then concentrated under reduced pressure, to thereby obtain 11.3 g of a concentrate. The concentrate was subjected to separation/purification through silica gel column chromatography (developing solution: ethyl acetate/hexane=3/1 (by volume)), to thereby obtain 6.52 g (17.9 mmol, yield: 74.9%) of N-t-butyl-hexahydro-2-oxo-3,5-methano-4H-cyclopenta[2,3-b]pyrrol-6-yl(2-methacryloyloxyethyl) carbamate.

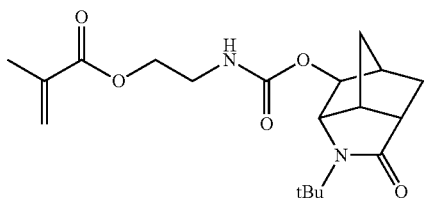 [SMILES: C=C(C)C(=O)OCCNC(=O)OC1C2CC3C(=O)N(C(C)(C)C)C1C3C2]

$^1$H-NMR (400 MHz, CDCl$_3$, TMS, ppm) δ: 6.12 (1H, s), 5.60 (1H, m), 4.94 (1H, br), 4.52 (1H, s), 4.24 (2H, t, J=5.2 Hz), 3.63 (1H, d, J=4.4 Hz), 3.51 (2H, dt, J=5.2, 5.2 Hz), 2.87 (1H, br), 2.49 (1H, br), 2.28 (1H, dd, J=10.4, 4.0 Hz), 1.95 (3H, m), 1.88 (1H, ddd, J=13.6, 10.8, 4.4 Hz), 1.79 (1H, d, J=10.8 Hz), 1.60 (1H, d, J=13.6 Hz), 1.36-1.45 (10H, m)

Synthesis Example 6

Synthesis of 5-hydroxy-3-methoxycarbonyl-2,6-norbornane carbolactone

To a three-necked flask having a capacity of 200 mL and equipped with a thermometer, a stirrer, and a nitrogen conduit, 16.7 g (0.102 mol) of bicyclo[2.2.1]hept-5-ene-2,3-dicarboxylic anhydride and 100.0 g of methanol were sequentially added, and the resultant mixture was heat-stirred under reflux of methanol for 20 hours. Thereafter, methanol was removed through evaporation under reduced pressure, to thereby obtain a concentrate.

To a four-necked flask having a capacity of 200 mL and equipped with a stirrer, a thermometer, and a dropping funnel, the entire amount of the above-obtained concentrate and 12.0 g (0.232 mol) of 88% formic acid were sequentially added and mixed, and then the resultant mixture was heated so as to attain an internal temperature of 45 to 46° C. Subsequently, 26.1 g (0.232 mol) of 30% aqueous hydrogen peroxide was added dropwise to the flask over 6 hours. After completion of the addition, the resultant mixture was further stirred at an internal temperature of 45° C. or thereabout for 20 hours. After cooling of the resultant reaction mixture to 15° C., sodium sulfite was added to the flask at an internal temperature of 15 to 20° C. until hydrogen peroxide was not detected by means of starch paper. Thereafter, the pH of the reaction mixture was adjusted to 7.8 with 20% aqueous sodium hydroxide solution. The reaction mixture was subjected to extraction thrice with 200 g of ethyl acetate, and the resultant organic layers were combined and concentrated under reduced pressure. 50 g Of ethyl acetate was added to the resultant solid, and the resultant mixture was heated to 60° C.

Thereafter, diisopropyl ether was slowly added to the mixture, and addition of diisopropyl ether was stopped when the resultant solution became turbid. Subsequently, the mixture was slowly cooled to 0° C., and the thus-precipitated crystals were separated through filtration. The crystals were washed with 30 g of diisopropyl ether at 0° C., and then dried under reduced pressure at 40° C. for 2 hours, to thereby obtain 10.0 g (purity: 99.0%, 0.047 mol) of 5-hydroxy-3-methoxycarbonyl-2,6-norbornane carbolactone.

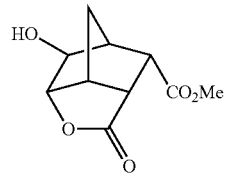

Example 6

Synthesis of 3-methoxycarbonyl-2,6-norbornane carbolacton-5-yl(2-methacryloyloxyethyl)carbamate To a three-necked flask having a capacity of 50 mL and equipped with a thermometer, a stirrer, and a nitrogen conduit, 5.00 g (23.6 mmol) of 5-hydroxy-3-methoxycarbonyl-2,6-norbornane carbolactone obtained in Synthesis Example 6, 15 mg of 4-acetamido-2,2,6,6-tetramethylpiperidine-N-oxyl, 30.0 g of ethyl acetate, and 0.18 g (1.18 mmol) of 1,8-diazabicyclo[5.4.0]undec-7-ene were added, and 4.2 g (27.1 mmol) of 2-methacryloyloxyethyl isocyanate was added dropwise to the flask under stirring at 24 to 26° C. over 0.5 hours. One hour after completion of the addition, the resultant reaction mixture was analyzed by means of an HPLC apparatus having a UV detector. As a result, the conversion of 5-hydroxy-3-methoxycarbonyl-2,6-norbornane carbolactone was found to be 69%. 20.0 g Of water was added to the reaction mixture, and the pH of the resultant mixture was adjusted to 1 with 1.0 wt % aqueous hydrochloric acid solution. Thereafter, the mixture was separated into an organic layer and an aqueous layer. The organic layer was washed six times with 20 g of water, and then the solvent was removed through evaporation under reduced pressure, to thereby obtain 9.13 g of a concentrate. The concentrate was subjected to separation/purification through silica gel column chromatography (developing solution: ethyl acetate/hexane=2/1 (by volume)), to thereby obtain 2.45 g (6.68 mmol, yield: 28.4%) of 3-methoxycarbonyl-2,6-norbornane carbolacton-5-yl(2-methacryloyloxyethyl)carbamate.

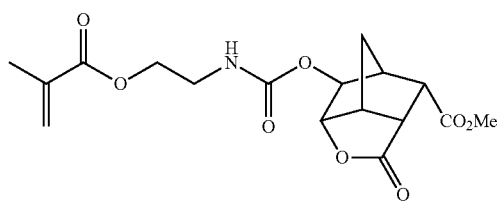 [SMILES: C=C(C)C(=O)OCCNC(=O)OC1C2CC3C1OC(=O)C3C2C(=O)OC]

$^1$H-NMR (400 MHz, CDCl$_3$, TMS, ppm) δ: 6.12 (1H, m), 5.60 (1H, m), 5.13 (2H, br), 4.61 (1H, d, J=4.8 Hz), 4.23 (2H, t, J=5.2 Hz), 3.72 (3H, s), 3.46-3.53 (2H, m), 3.30 (1H, br), 3.09 (1H, dd, J=10.8, 3.2 Hz), 2.77-2.85 (2H, m), 2.06 (1H, d, J=11.6 Hz), 1.95 (3H, m), 1.65 (1H, d, J=11.6 Hz)

Example 7

Synthesis of Polymer (a)

To a three-necked flask having a capacity of 50 mL and equipped with a stirrer, a reflux condenser, and a thermometer, 4.0 g (17.2 mmol) of 2-methacryloyloxy-2-methyladamantane, 1.4 g (6.0 mmol) of 3-hydroxyadamantan-1-yl methacrylate, 6.8 g (19.8 mmol) of 2,6-norbornane sulton-5-yl(2-methacryloyloxyethyl)carbamate obtained in Example 1, and 36.4 g of methyl ethyl ketone were added, and nitrogen bubbling was carried out for 10 minutes. Under nitrogen atmosphere, 0.36 g (2 mmol) of 2,2'-azobisisobutyronitrile was added to the flask, and polymerization reaction was carried out at 80° C. for 4 hours. The resultant reaction mixture was added dropwise to 220 g of methanol at room temperature under stirring, and the obtained precipitate was separated through filtration. The precipitate was dried under reduced pressure (26.7 Pa) at 50° C. for 8 hours, to thereby obtain 7.6 g of a polymer (a) having the below-described repeating units (each numerical value represents a mole fraction). The polymer (a) was found to have a weight average molecular weight (Mw) of 9,200 and a molecular weight distribution of 1.9.

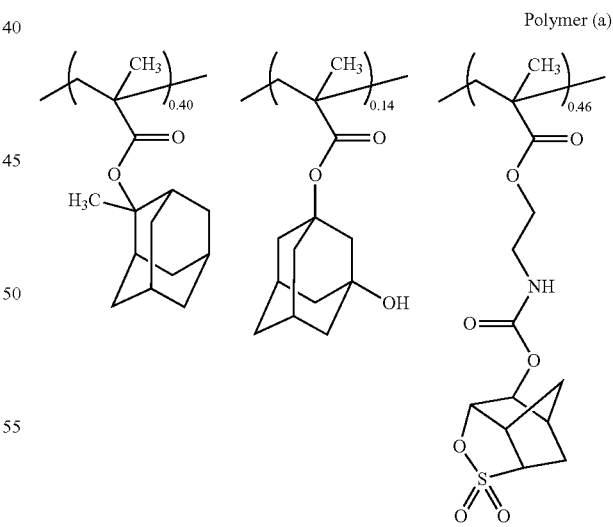

Polymer (a)

Example 8

Synthesis of Polymer (b)

To a three-necked flask having a capacity of 50 mL and equipped with a stirrer, a reflux condenser, and a thermometer, 4.0 g (17.2 mmol) of 2-methacryloyloxy-2-methyladamantane, 1.4 g (6.0 mmol) of 3-hydroxyadamantan-1-yl methacrylate, 6.1 g (19.8 mmol) of 2,6-norbornane carbolacton-5-yl(2-methacryloyloxyethyl)carbamate obtained in Example 2, and 36.4 g of methyl ethyl ketone were added, and nitrogen bubbling was carried out for 10 minutes. Under nitrogen atmosphere, 0.36 g (2 mmol) of 2,2'-azobisisobutyronitrile was added to the flask, and polymerization reaction was carried out at 80° C. for 4 hours. The resultant reaction mixture was added dropwise to 220 g of methanol at room temperature under stirring, and the obtained precipitate was separated through filtration. The precipitate was dried under reduced pressure (26.7 Pa) at 50° C. for 8 hours, to thereby obtain 7.8 g of a polymer (b) having the below-described repeating units (each numerical value represents a mole fraction). The polymer (b) was found to have a weight average molecular weight (Mw) of 8,900 and a molecular weight distribution of 1.8.

Polymer (b)

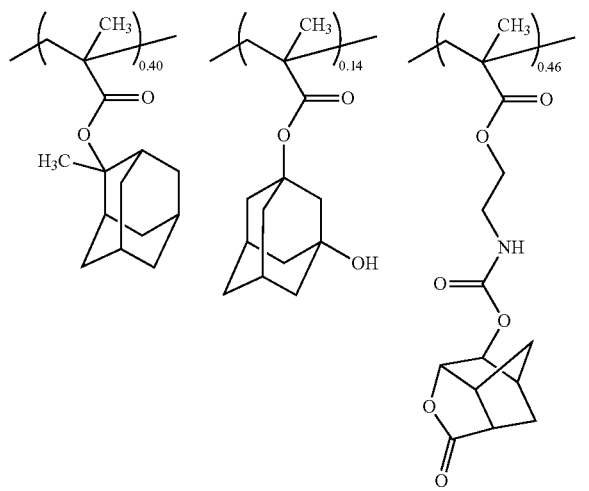

Example 9

Synthesis of Polymer (c)

To a three-necked flask having a capacity of 50 mL and equipped with a stirrer, a reflux condenser, and a thermometer, 4.0 g (17.2 mmol) of 2-methacryloyloxy-2-methyladamantane, 1.4 g (6.0 mmol) of 3-hydroxyadamantan-1-yl methacrylate, 6.2 g (19.8 mmol) of 2,6-(7-oxanorbornane) carbolacton-5-yl(2-methacryloyloxyethyl)carbamate obtained in Example 3, and 36.4 g of methyl ethyl ketone were added, and nitrogen bubbling was carried out for 10 minutes. Under nitrogen atmosphere, 0.36 g (2 mmol) of 2,2'-azobisisobutyronitrile was added to the flask, and polymerization reaction was carried out at 80° C. for 4 hours. The resultant reaction mixture was added dropwise to 220 g of methanol at room temperature under stirring, and the obtained precipitate was separated through filtration. The precipitate was dried under reduced pressure (26.7 Pa) at 50° C. for 8 hours, to thereby obtain 7.2 g of a polymer (c) having the below-described repeating units (each numerical value represents a mole fraction). The polymer (c) was found to have a weight average molecular weight (Mw) of 9,400 and a molecular weight distribution of 1.9.

Polymer (c)

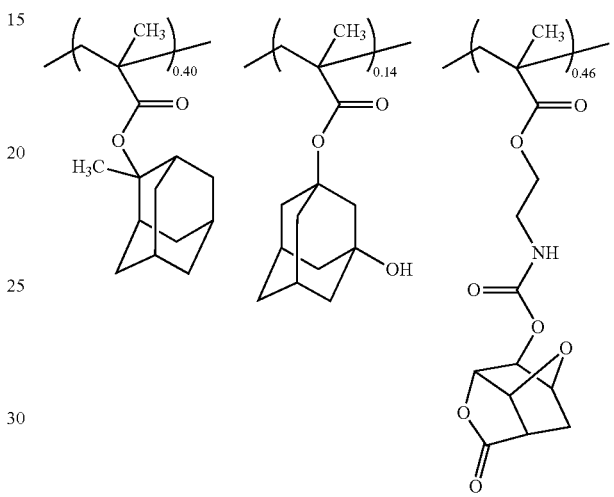

Example 10

Synthesis of Polymer (d)

To a three-necked flask having a capacity of 50 mL and equipped with a stirrer, a reflux condenser, and a thermometer, 4.0 g (17.2 mmol) of 2-methacryloyloxy-2-methyladamantane, 1.4 g (6.0 mmol) of 3-hydroxyadamantan-1-yl methacrylate, 6.9 g (19.8 mmol) of 7-oxanorbornane-2,6-sulton-5-yl(2-methacryloyloxyethyl)carbamate obtained in Example 4, and 36.4 g of methyl ethyl ketone were added, and nitrogen bubbling was carried out for 10 minutes. Under nitrogen atmosphere, 0.36 g (2 mmol) of 2,2'-azobisisobutyronitrile was added to the flask, and polymerization reaction was carried out at 80° C. for 4 hours. The resultant reaction mixture was added dropwise to 220 g of methanol at room temperature under stirring, and the obtained precipitate was separated through filtration. The precipitate was dried under reduced pressure (26.7 Pa) at 50° C. for 8 hours, to thereby obtain 6.9 g of a polymer (d) having the below-described repeating units (each numerical value represents a mole fraction). The polymer (d) was found to have a weight average molecular weight (Mw) of 8,800 and a molecular weight distribution of 1.8.

Example 11

Synthesis of Polymer (e)

To a three-necked flask having a capacity of 50 mL and equipped with a stirrer, a reflux condenser, and a thermometer, 4.0 g (17.2 mmol) of 2-methacryloyloxy-2-methyladamantane, 1.4 g (6.0 mmol) of 3-hydroxyadamantan-1-yl methacrylate, 7.2 g (19.8 mmol) of N-t-butyl-hexahydro-2-oxo-3,5-methano-4H-cyclopenta[2,3-b]pyrrol-6-yl(2-methacryloyloxyethyl)carbamate obtained in Example 5, and 36.4 g of methyl ethyl ketone were added, and nitrogen bubbling was carried out for 10 minutes. Under nitrogen atmosphere, 0.36 g (2 mmol) of 2,2'-azobisisobutyronitrile was added to the flask, and polymerization reaction was carried out at 80° C. for 4 hours. The resultant reaction mixture was added dropwise to 220 g of methanol at room temperature under stirring, and the obtained precipitate was separated through filtration. The precipitate was dried under reduced pressure (26.7 Pa) at 50° C. for 8 hours, to thereby obtain 7.0 g of a polymer (e) having the below-described repeating units (each numerical value represents a mole fraction). The polymer (e) was found to have a weight average molecular weight (Mw) of 10,100 and a molecular weight distribution of 1.8.

Example 12

Synthesis of Polymer (f)

To a three-necked flask having a capacity of 50 mL and equipped with a stirrer, a reflux condenser, and a thermometer, 4.0 g (17.2 mmol) of 2-methacryloyloxy-2-methyladamantane, 1.4 g (6.0 mmol) of 3-hydroxyadamantan-1-yl methacrylate, 7.3 g (19.8 mmol) of 3-methoxycarbonyl-2,6-norbornane carbolacton-5-yl(2-methacryloyloxyethyl)carbamate obtained in Example 6, and 36.4 g of methyl ethyl ketone were added, and nitrogen bubbling was carried out for 10 minutes. Under nitrogen atmosphere, 0.36 g (2 mmol) of 2,2'-azobisisobutyronitrile was added to the flask, and polymerization reaction was carried out at 80° C. for 4 hours. The resultant reaction mixture was added dropwise to 220 g of methanol at room temperature under stirring, and the obtained precipitate was separated through filtration. The precipitate was dried under reduced pressure (26.7 Pa) at 50° C. for 8 hours, to thereby obtain 6.6 g of a polymer (f) having the below-described repeating units (each numerical value represents a mole fraction). The polymer (f) was found to have a weight average molecular weight (Mw) of 9,200 and a molecular weight distribution of 1.7.

Comparative Synthesis Example 1

Synthesis of Polymer (g)

To a three-necked flask having a capacity of 50 mL and equipped with a stirrer, a reflux condenser, and a thermometer, 4.0 g (17.2 mmol) of 2-methacryloyloxy-2-methyladamantane, 1.4 g (6.0 mmol) of 3-hydroxyadamantan-1-yl methacrylate, 6.3 g (19.8 mmol) of 5-(methacryloyloxyacetoxy)-2,6-norbornane sultone, and 36.4 g of methyl ethyl ketone were added, and nitrogen bubbling was carried out for 10 minutes. Under nitrogen atmosphere, 0.36 g (2 mmol) of 2,2'-azobisisobutyronitrile was added to the flask, and polymerization reaction was carried out at 80° C. for 4 hours. The resultant reaction mixture was added dropwise to 220 g of methanol at room temperature under stirring, and the obtained precipitate was separated through filtration. The precipitate was dried under reduced pressure (26.7 Pa) at 50° C. for 8 hours, to thereby obtain 7.3 g of a polymer (g) having the below-described repeating units (each numerical value represents a mole fraction). The polymer (g) was found to have a weight average molecular weight (Mw) of 9,400 and a molecular weight distribution of 1.9.

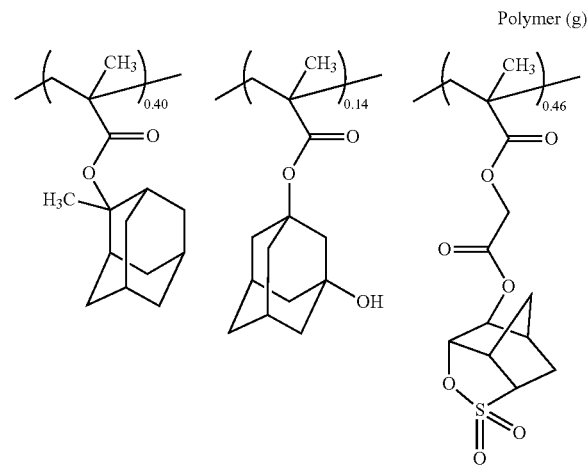

Polymer (g)

Comparative Synthesis Example 2

Synthesis of Polymer (h)

To a three-necked flask having a capacity of 50 mL and equipped with a stirrer, a reflux condenser, and a thermometer, 4.0 g (17.2 mmol) of 2-methacryloyloxy-2-methyladamantane, 1.4 g (6.0 mmol) of 3-hydroxyadamantan-1-yl methacrylate, 5.5 g (19.8 mmol) of 5-(methacryloyloxyacetoxy)-2,6-norbornane carbolactone, and 36.4 g of methyl ethyl ketone were added, and nitrogen bubbling was carried out for 10 minutes. Under nitrogen atmosphere, 0.36 g (2 mmol) of 2,2'-azobisisobutyronitrile was added to the flask, and polymerization reaction was carried out at 80° C. for 4 hours. The resultant reaction mixture was added dropwise to 220 g of methanol at room temperature under stirring, and the obtained precipitate was separated through filtration. The precipitate was dried under reduced pressure (26.7 Pa) at 50° C. for 8 hours, to thereby obtain 7.0 g of a polymer (h) having the below-described repeating units (each numerical value represents a mole fraction). The polymer (h) was found to have a weight average molecular weight (Mw) of 8,900 and a molecular weight distribution of 1.8.

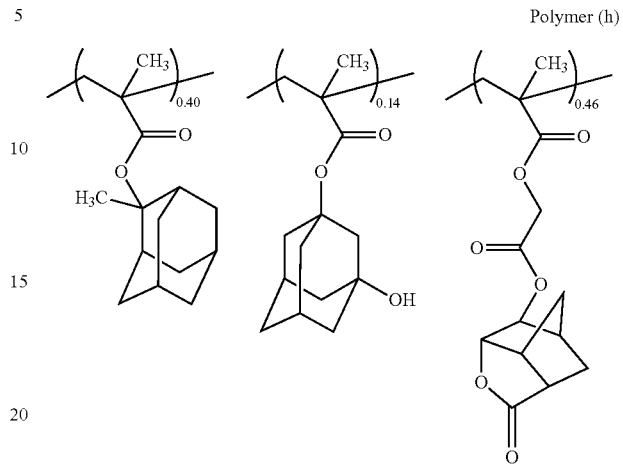

Polymer (h)

Examples 13 to 18 and Comparative Examples 1 and 2

100 Parts by mass of each of the polymers (a), (b), (c), (d), (e), (f), (g), and (h) obtained in Examples 7 to 12 and Comparative Synthesis Examples 1 and 2 was mixed with 4.5 parts by mass of "TPS-109" (trade name, component: triphenylsulfonium nonafluoro-n-butanesulfonate, product of Midori Kagaku Co., Ltd.) serving as a photoacid generator, and 1896 parts by mass of a solvent mixture of propylene glycol monomethyl ether acetate/cyclohexanone (1:1 by mass) serving as a solvent. Thus, eight photoresist compositions were prepared.

Each photoresist composition was separated through filtration with a membrane filter having a pore size of 0.2 μm. 6 Mass % solution of cresol novolac resin ("PS-6937," product of Gunei Chemical Industry Co., Ltd.) in propylene glycol monomethyl ether acetate was coated onto a silicon wafer having a diameter of 10 cm through spin coating, and then baking was carried out on a hot plate at 200° C. for 90 seconds, to thereby form, on the wafer, an anti-reflection film (underlayer) having a thickness of 100 nm. The above-obtained filtrate was coated onto the wafer having the film thereon through spin coating, and prebaking was carried out on a hot plate at 130° C. for 90 seconds, to thereby form a resist film having a thickness of 300 nm. The resist film was subjected to two-beam interference exposure with ArF excimer laser having a wavelength of 193 nm. Subsequently, post-exposure baking was carried out at 130° C. for 90 seconds, and then the resultant wafer was developed with 2.38 mass % aqueous tetramethylammonium hydroxide solution for 60 seconds, to thereby form a 1:1 line and space pattern. The thus-developed wafer was cut and observed under a scanning electron microscope (SEM). There was observed the shape of the pattern with respect to exposure light for forming a 1:1 line and space having a line width of 100 nm. Also, line width roughness (LWR) was determined.

For determination of LWR, line widths were measured at a plurality of points in a measurement monitor, and the variance (3σ) of the line widths at the points was employed as an index. The shape of a cross section profile of the pattern-formed layer was observed under a scanning electron microscope (SEM) and evaluated as follows. When the patterned cross section shape had high squareness, rating "○" was assigned, whereas when the patterned cross section shape had low squareness, rating "x" was assigned. The results are shown in Tables 1 and 2.

TABLE 1

| | Evaluation by exposure | | |
|---|---|---|---|
| | Polymer employed | LWR (nm) | Pattern shape |
| Example 13 | Polymer (a) | 8.2 | ○ |
| Example 14 | Polymer (b) | 9.3 | ○ |
| Example 15 | Polymer (c) | 8.8 | ○ |
| Example 16 | Polymer (d) | 8.0 | ○ |
| Example 17 | Polymer (e) | 9.0 | ○ |
| Example 18 | Polymer (f) | 9.1 | ○ |

TABLE 2

| | Evaluation by exposure | | |
|---|---|---|---|
| | Polymer employed | LWR (nm) | Pattern shape |
| Comparative Example 1 | Polymer (g) | 10.4 | ○ |
| Comparative Example 2 | Polymer (h) | 11.2 | x |

As is clear from the aforementioned data, a resist composition containing each of the polymers (a) to (f), the polymer being produced through polymerization of a raw material containing the acrylic ester derivative (1) of the present invention, realizes formation of a resist pattern having a favorable shape and improved LWR, as compared with the case of a resist composition containing each of the polymers (g) and (h), the polymer being produced through polymerization of a raw material not containing the acrylic ester derivative (1) of the present invention. That is, the resist composition of the present invention can form a resist pattern having both high resolution and low LWR.

INDUSTRIAL APPLICABILITY

The acrylic ester derivative of the present invention is useful as a raw material of a polymer for a resist composition which realizes formation of a resist pattern having a favorable shape and improved LWR.

The invention claimed is:

1. An acrylic ester derivative of formula (1):

wherein
$R^1$ is a hydrogen atom, a methyl group, or a trifluoromethyl group;
$R^2$, $R^3$, $R^5$, $R^7$, $R^8$, and $R^{10}$ are each independently a hydrogen atom, a C1 to C6 alkyl group, a C3 to C6 cycloalkyl group, or a C1 to C6 alkoxy group;
$R^4$ and $R^6$ are each independently a hydrogen atom, a C1 to C6 alkyl group, a C3 to C6 cycloalkyl group, or a C1 to C6 alkoxy group, or $R^4$ and $R^6$ are linked together to form a C1 to C3 alkylene group, —O—, or —S—;
$R^9$ is a hydrogen atom, a C1 to C6 alkyl group, a C3 to C6 cycloalkyl group, a C1 to C6 alkoxy group, or —COOR$^{11}$, wherein $R^{11}$ is a C1 to C3 alkyl group;
X is —O—;
Y is —S(=O)$_n$—, n is an integer of from 0 to 2; and
$R^8$ and $R^9$ are each independently in an endo or exo position.

2. The acrylic ester derivative of claim 1, having formula (1'):

wherein Z is a methylene group, —O—, or —S—.

3. The acrylic ester derivative of claim 1, wherein $R^1$ is a hydrogen atom or a methyl group.

4. The acrylic ester derivative of claim 1, wherein $R^2$, $R^3$, $R^5$, $R^7$, $R^8$, and $R^{10}$ are each independently a hydrogen, a C1 to C6 alkyl group, a C3 to C6 cycloalkyl group, or a C1 to C6 alkoxy group,
wherein
the C1 to C6 alkyl group is at least one selected from the group consisting of methyl, ethyl, n-propyl, isopropyl, n-butyl, isobutyl, s-butyl, n-pentyl, and n-hexyl,
the C3 to C6 cycloalkyl group is at least one selected from the group consisting of cyclopropyl, cyclobutyl, cyclopentyl, and cyclohexyl, and
the C1 to C6 alkoxy group is at least one selected from the group consisting of methoxy, ethoxy, n-propoxy, isopropoxy, n-butoxy, isobutoxy, t-butoxy, n-pentyloxy, and n-hexyloxy.

5. The acrylic ester derivative of claim 1, wherein $R^2$, $R^3$, $R^5$, $R^7$, $R^8$, and $R^{10}$ are each independently a hydrogen atom, a C1 to C3 alkyl group, or a C1 to C3 alkoxy group.

6. The acrylic ester derivative of claim 1, wherein $R^2$, $R^3$, $R^5$, $R^7$, $R^8$, and $R^{10}$ are each independently a hydrogen atom.

7. The acrylic ester derivative of claim 1, wherein $R^4$ and $R^6$ are each independently a hydrogen atom, a C1 to C6 alkyl group, a C3 to C6 cycloalkyl group, or a C1 to C6 alkoxy group.

8. The acrylic ester derivative of claim 7,
wherein
the C1 to C6 alkyl group is at least one selected from the group consisting of methyl, ethyl, n-propyl, isopropyl, n-butyl, isobutyl, s-butyl, n-pentyl, and n-hexyl,
the C3 to C6 cycloalkyl group is at least one selected from the group consisting of cyclopropyl, cyclobutyl, cyclopentyl, and cyclohexyl, and
the C1 to C6 alkoxy group is at least one selected from the group consisting of methoxy, ethoxy, n-propoxy, isopropoxy, n-butoxy, isobutoxy, t-butoxy, n-pentyloxy, and n-hexyloxy.

9. The acrylic ester derivative of claim 7, wherein $R^4$ and $R^6$ are each independently a hydrogen atom, a C1 to C3 alkyl group, a C3 to C6 cycloalkyl group, or a C1 to C3 alkoxy group.

10. The acrylic ester derivative of claim 1, wherein $R^4$ and $R^6$ are linked together to form a C1 to C3 alkylene group, —O—, or —S—.

11. The acrylic ester derivative of claim 10, wherein $R^4$ and $R^6$ are linked together to form a C1 to C3 alkylene group, wherein the C1 to C3 alkylene group is selected from the group consisting of methylene, ethane-1,1-diyl, ethane-1,2-diyl, propane-1,1-diyl, propane-1,2-diyl, propane-1,3-diyl, and propane-2,2-diyl.

12. The acrylic ester derivative of claim 11, wherein the C1 to C3 alkylene group is a methylene group or an ethane-1,2-diyl group.

13. The acrylic ester derivative of claim 11, wherein the C1 to C3 alkylene group is a methylene group.

14. The acrylic ester derivative of claim 1, wherein $R^9$ is in an endo position.

15. An acrylic ester derivative of formula (1):

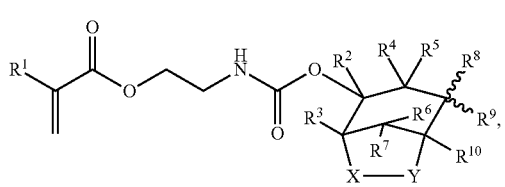
(1)

wherein
- $R^1$ is a hydrogen atom, a methyl group, or a trifluoromethyl group;
- $R^2, R^3, R^5, R^7, R^8$, and $R^{10}$ are each independently a hydrogen atom, a C1 to C6 alkyl group, a C3 to C6 cycloalkyl group, or a C1 to C6 alkoxy group;
- $R^4$ and $R^6$ are each independently a hydrogen atom, a C1 to C6 alkyl group, a C3 to C6 cycloalkyl group, or a C1 to C6 alkoxy group, or $R^4$ and $R^6$ are linked together to form a C1 to C3 alkylene group, —O—, or —S—;
- $R^9$ is a hydrogen atom, a C1 to C6 alkyl group, a C3 to C6 cycloalkyl group, a C1 to C6 alkoxy group, or —COOR$^{11}$, wherein $R^{11}$ is a C1 to C3 alkyl group;
- X is —N($R^{12}$)—, wherein $R^{12}$ is a hydrogen atom or a C1 to C5 alkyl group;
- Y is —C(=O)—; and
- $R^8$ and $R^9$ are each independently in an endo or exo position.

16. The acrylic ester derivative of claim 15, wherein $R^{12}$ is a branched C3 or C4 alkyl group.

17. The acrylic ester derivative of claim 15, wherein $R^{12}$ is a tert-butyl group.

18. A polymer comprising the acrylic ester derivative of claim 1 in polymerized form.

19. A photoresist composition comprising:
the polymer of claim 18, a photoacid generator, and a solvent.

20. A method for producing the acrylic ester derivative of claim 1, the method comprising reacting an isocyanate derivative of formula (2):

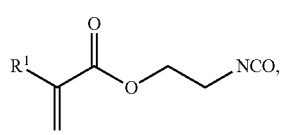
(2)

with an alcohol derivative of formula (3):

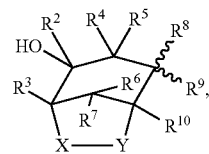
(3)

at a temperature of from −30 to 100° C.

* * * * *